United States Patent
Schwartz et al.

(10) Patent No.: US 11,350,996 B2
(45) Date of Patent: Jun. 7, 2022

(54) CHARACTERISTIC TRACK CATHETER NAVIGATION

(71) Applicant: Navix International Limited, Road Town (VG)

(72) Inventors: Yitzhack Schwartz, Haifa (IL); Eli Dichterman, Haifa (IL); Zalman Ibragimov, Rehovot (IL); Yehonatan Ben David, Tel-Aviv (IL)

(73) Assignee: Navix International Limited, Road Town (VG)

( * ) Notice: Subject to any disclaimer, the term of this patent is extended or adjusted under 35 U.S.C. 154(b) by 635 days.

(21) Appl. No.: 16/317,548

(22) PCT Filed: Jul. 14, 2017

(86) PCT No.: PCT/IB2017/054263
§ 371 (c)(1),
(2) Date: Jan. 13, 2019

(87) PCT Pub. No.: WO2018/011757
PCT Pub. Date: Jan. 18, 2018

(65) Prior Publication Data
US 2019/0307514 A1   Oct. 10, 2019

Related U.S. Application Data

(60) Provisional application No. 62/449,055, filed on Jan. 22, 2017, provisional application No. 62/362,146, filed on Jul. 14, 2016.

(51) Int. Cl.
*A61B 34/20*   (2016.01)
*A61B 5/06*   (2006.01)
(Continued)

(52) U.S. Cl.
CPC ............... *A61B 34/20* (2016.02); *A61B 5/06* (2013.01); *A61B 5/063* (2013.01); *A61B 5/743* (2013.01);
(Continued)

(58) Field of Classification Search
CPC ......... A61B 34/20; A61B 18/00; A61B 5/743; A61B 5/06; A61B 5/063; A61B 5/6852;
(Continued)

(56) References Cited

U.S. PATENT DOCUMENTS

| 4,917,097 A | 4/1990 | Proudian et al. |
| 5,553,611 A | 9/1996 | Budd et al. |

(Continued)

FOREIGN PATENT DOCUMENTS

| CA | 2237992 | 3/1998 |
| EP | 0974936 | 1/2000 |

(Continued)

OTHER PUBLICATIONS

International Preliminary Report on Patentability dated Jan. 24, 2019 From the International Bureau of WIPO Re. Application No. PCT/IB2017/054263. (8 Pages).
(Continued)

*Primary Examiner* — Oommen Jacob

(57) ABSTRACT

Registration of catheter-sensed intrabody voltage field measurements obtained along one or more tracks of catheter advance of withdrawal is made, in some embodiments, to reference voltage field measurements lying along predetermined tracks. Tracks optionally comprise the course of a blood vessel such as the superior or inferior vena cava, a path defined and/or limited by encounters with a wall of a heart chamber and/or apertures thereof, and/or another track of catheter motion. In some embodiments, transform param-
(Continued)

eters are propagated to regions away from the track, potentially allowing more rapid acquisition of targets.

29 Claims, 10 Drawing Sheets

(51) Int. Cl.
  *A61B 18/00* (2006.01)
  *A61M 25/01* (2006.01)
  *A61B 5/00* (2006.01)

(52) U.S. Cl.
  CPC ......... *A61B 18/00* (2013.01); *A61M 25/0105* (2013.01); *A61B 5/6852* (2013.01); *A61B 2018/00351* (2013.01); *A61B 2018/00577* (2013.01); *A61B 2018/00904* (2013.01); *A61B 2034/2053* (2016.02); *A61M 2025/0166* (2013.01)

(58) Field of Classification Search
  CPC A61B 2018/00351; A61B 2018/00577; A61B 2034/2053; A61B 2018/00904; A61B 5/05; A61B 8/5238; A61B 5/066; A61B 5/6876; A61B 5/7285; A61B 8/12; A61B 6/5247; A61B 8/4254; A61B 8/4245; A61B 5/062; A61B 6/12; A61B 5/0066; A61B 6/504; A61B 5/055; A61B 5/318; A61B 2034/2051; A61M 25/0105; A61M 2025/0166; A61M 25/0108
  See application file for complete search history.

(56) References Cited

U.S. PATENT DOCUMENTS

| | | | |
|---|---|---|---|
| 5,634,469 A * | 6/1997 | Bruder | A61B 5/282 |
| | | | 600/512 |
| 5,662,108 A | 9/1997 | Budd et al. | |
| 5,697,377 A | 12/1997 | Wittkampf | |
| 5,724,978 A | 3/1998 | Tenhoff | |
| 5,983,126 A | 11/1999 | Wittkampf | |
| 6,010,500 A * | 1/2000 | Sherman | A61B 18/1492 |
| | | | 606/41 |
| 6,019,725 A | 2/2000 | Vesely et al. | |
| 6,038,468 A | 3/2000 | Rex | |
| 6,064,904 A * | 5/2000 | Yanof | A61B 90/36 |
| | | | 606/130 |
| 6,240,307 B1 | 5/2001 | Beatty et al. | |
| 6,266,552 B1 | 7/2001 | Slettenmark | |
| 6,317,621 B1 | 11/2001 | Graumann et al. | |
| 6,322,558 B1 | 11/2001 | Taylor et al. | |
| 6,423,057 B1 | 7/2002 | He et al. | |
| 6,515,657 B1 | 2/2003 | Zanelli | |
| 6,640,119 B1 | 10/2003 | Budd et al. | |
| 6,728,562 B1 | 4/2004 | Budd et al. | |
| 6,826,420 B1 | 11/2004 | Beatty et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,187,973 B2 | 3/2007 | Hauck | |
| 7,189,208 B1 | 3/2007 | Beatty et al. | |
| 7,881,769 B2 | 2/2011 | Sobe | |
| 7,996,060 B2 | 8/2011 | Trofimov et al. | |
| 2002/0068931 A1 | 6/2002 | Wong et al. | |
| 2002/0137014 A1 * | 9/2002 | Anderson | G16H 50/50 |
| | | | 434/262 |
| 2003/0074011 A1 | 4/2003 | Gilboa et al. | |
| 2003/0220636 A1 | 11/2003 | Bowman et al. | |
| 2004/0039278 A1 | 2/2004 | Wacker et al. | |
| 2004/0044279 A1 | 3/2004 | Lewin et al. | |
| 2004/0097805 A1 | 5/2004 | Verard et al. | |
| 2004/0097806 A1 * | 5/2004 | Hunter | A61B 1/00071 |
| | | | 600/434 |
| 2004/0147920 A1 | 7/2004 | Keidar | |
| 2004/0176804 A1 | 9/2004 | Palti | |
| 2005/0015006 A1 | 1/2005 | Mitschke et al. | |
| 2005/0033164 A1 | 2/2005 | Yatsuo et al. | |
| 2005/0054913 A1 | 3/2005 | Duerk et al. | |
| 2005/0054918 A1 | 3/2005 | Sra | |
| 2005/0058328 A1 | 3/2005 | Moreau-Gobard | |
| 2005/0182319 A1 * | 8/2005 | Glossop | A61B 8/481 |
| | | | 600/424 |
| 2005/0245814 A1 | 11/2005 | Anderson et al. | |
| 2006/0079759 A1 * | 4/2006 | Vaillant | A61B 90/36 |
| | | | 600/424 |
| 2006/0089552 A1 | 4/2006 | Goldbach | |
| 2006/0241401 A1 | 10/2006 | Govari et al. | |
| 2006/0253116 A1 * | 11/2006 | Avitall | A61M 25/0147 |
| | | | 606/41 |
| 2007/0043296 A1 | 2/2007 | Schwartz | |
| 2007/0049915 A1 | 3/2007 | Haemmerich et al. | |
| 2007/0066889 A1 * | 3/2007 | Boese | A61B 5/053 |
| | | | 600/424 |
| 2007/0106289 A1 | 5/2007 | O'Sullivan | |
| 2007/0167706 A1 | 7/2007 | Boese et al. | |
| 2007/0167726 A1 | 7/2007 | Unai et al. | |
| 2007/0232886 A1 * | 10/2007 | Camus | A61B 6/12 |
| | | | 600/407 |
| 2008/0114235 A1 | 5/2008 | Unai et al. | |
| 2008/0118135 A1 | 5/2008 | Averbuch et al. | |
| 2008/0125775 A1 | 5/2008 | Morris | |
| 2008/0139930 A1 * | 6/2008 | Weese | A61B 6/4441 |
| | | | 600/424 |
| 2008/0177175 A1 | 7/2008 | Mottola et al. | |
| 2008/0183070 A1 | 7/2008 | Unai et al. | |
| 2008/0190438 A1 * | 8/2008 | Harlev | A61B 5/0538 |
| | | | 128/898 |
| 2008/0208031 A1 | 8/2008 | Kurpad et al. | |
| 2008/0221425 A1 | 9/2008 | Olson et al. | |
| 2008/0275440 A1 | 11/2008 | Kratoska et al. | |
| 2008/0275465 A1 | 11/2008 | Paul et al. | |
| 2008/0294034 A1 * | 11/2008 | Krueger | A61B 90/36 |
| | | | 600/409 |
| 2009/0010519 A1 | 1/2009 | Wakai et al. | |
| 2009/0015818 A1 | 1/2009 | Ikeda et al. | |
| 2009/0148012 A1 | 6/2009 | Altmann et al. | |
| 2009/0171274 A1 | 7/2009 | Harlev et al. | |
| 2009/0221908 A1 | 9/2009 | Glossop | |
| 2009/0225077 A1 | 9/2009 | Sudarsky et al. | |
| 2009/0262109 A1 | 10/2009 | Markowitz et al. | |
| 2009/0275828 A1 | 11/2009 | Shachar et al. | |
| 2009/0281566 A1 | 11/2009 | Edwards et al. | |
| 2010/0063400 A1 | 3/2010 | Hall et al. | |
| 2010/0106154 A1 * | 4/2010 | Harlev | A61B 5/063 |
| | | | 606/41 |
| 2010/0217116 A1 | 8/2010 | Eck et al. | |
| 2010/0249579 A1 | 9/2010 | Starks | |
| 2010/0274239 A1 | 10/2010 | Paul et al. | |
| 2010/0283484 A1 * | 11/2010 | Cohen | A61B 5/063 |
| | | | 324/649 |
| 2010/0312094 A1 | 12/2010 | Guttman et al. | |
| 2011/0106221 A1 | 5/2011 | Neal, II et al. | |
| 2011/0230758 A1 * | 9/2011 | Eichler | A61B 5/6852 |
| | | | 600/424 |
| 2011/0282186 A1 | 11/2011 | Harlev et al. | |
| 2012/0059249 A1 * | 3/2012 | Verard | A61B 6/463 |
| | | | 600/424 |
| 2012/0070046 A1 * | 3/2012 | Wu | G06T 7/20 |
| | | | 382/128 |
| 2012/0078129 A1 | 3/2012 | Bailin | |
| 2012/0109115 A1 | 5/2012 | Condie et al. | |
| 2012/0123250 A1 | 5/2012 | Pang et al. | |
| 2012/0150046 A1 | 6/2012 | Watson et al. | |
| 2012/0172724 A1 | 7/2012 | Hill et al. | |
| 2012/0173217 A1 | 7/2012 | Heimbecher | |
| 2012/0197243 A1 | 8/2012 | Sherman et al. | |
| 2012/0238866 A1 | 9/2012 | Wang et al. | |
| 2013/0079628 A1† | 3/2013 | Groszmann | |
| 2013/0137980 A1 | 5/2013 | Waters et al. | |

(56) References Cited

U.S. PATENT DOCUMENTS

| | | | |
|---|---|---|---|
| 2013/0245429 A1* | 9/2013 | Zhang | A61B 6/485 600/424 |
| 2013/0272593 A1 | 10/2013 | Lee et al. | |
| 2013/0310673 A1 | 11/2013 | Govari et al. | |
| 2014/0024911 A1 | 1/2014 | Harlev et al. | |
| 2014/0088943 A1 | 3/2014 | Trayanova et al. | |
| 2014/0187949 A1 | 7/2014 | Zhao et al. | |
| 2014/0243641 A1 | 8/2014 | Boveja et al. | |
| 2014/0243813 A1 | 8/2014 | Paul et al. | |
| 2014/0275991 A1 | 9/2014 | Potter et al. | |
| 2014/0330111 A1 | 11/2014 | Lichtenstein et al. | |
| 2015/0080762 A1 | 3/2015 | Kassab et al. | |
| 2015/0099942 A1 | 4/2015 | Edouard | |
| 2015/0223757 A1 | 8/2015 | Werneth et al. | |
| 2015/0320515 A1* | 11/2015 | Edwards | A61B 5/064 600/407 |
| 2016/0095651 A1 | 4/2016 | Deno et al. | |
| 2016/0095653 A1 | 4/2016 | Lambert et al. | |
| 2016/0242667 A1 | 8/2016 | Fay et al. | |
| 2016/0270683 A1 | 9/2016 | Grass et al. | |
| 2017/0014181 A1 | 1/2017 | Bar-Tai et al. | |
| 2017/0156792 A1 | 6/2017 | Ziv-Ari et al. | |
| 2018/0153437 A1 | 6/2018 | Schwartz et al. | |
| 2018/0240237 A1* | 8/2018 | Donhowe | A61B 34/30 |
| 2019/0254564 A1 | 8/2019 | Schwartz et al. | |
| 2019/0307514 A1* | 10/2019 | Schwartz | A61B 18/00 |

FOREIGN PATENT DOCUMENTS

| | | | |
|---|---|---|---|
| EP | 1472975 | 11/2004 | |
| EP | 1853162 | 11/2004 | |
| EP | 1504713 | 2/2005 | |
| EP | 1726268 | 11/2006 | |
| EP | 1767166 | 3/2007 | |
| EP | 1943974 | 7/2008 | |
| EP | 2075763 | 7/2009 | |
| EP | 2248480 | 11/2010 | |
| EP | 2712543 | 4/2014 | |
| EP | 2777584 | 9/2014 | |
| HR | P20131208 | 3/2014 | |
| JP | 2001-340336 | 12/2001 | |
| WO | WO 97/29682 | 8/1997 | |
| WO | WO 98/01069 | 1/1998 | |
| WO | WO-2007042986 A2 * | 4/2007 | A61B 90/10 |
| WO | WO 2007/067628 | 6/2007 | |
| WO | WO 2008/097767 | 8/2008 | |
| WO | WO 2008/104914 | 9/2008 | |
| WO | WO 2010/102794 | 9/2010 | |
| WO | WO 2010/129095 | 11/2010 | |
| WO | WO 2011/142931 | 11/2011 | |
| WO | WO 2012/092016 | 7/2012 | |
| WO | WO 2013/192598 | 12/2013 | |
| WO | 2014091418 A1 † | 6/2014 | |
| WO | WO 2014/118535 | 8/2014 | |
| WO | WO 2014/182822 | 11/2014 | |
| WO | WO 2016/038499 | 3/2016 | |
| WO | WO 2016/088084 | 6/2016 | |
| WO | WO 2016/135584 | 9/2016 | |
| WO | WO 2016/181315 | 11/2016 | |
| WO | WO 2016/181316 | 11/2016 | |
| WO | WO 2016/181317 | 11/2016 | |
| WO | WO 2016/181318 | 11/2016 | |
| WO | WO 2016/181320 | 11/2016 | |
| WO | WO 2018/011757 | 1/2018 | |
| WO | WO 2018/011757 A9 | 1/2018 | |
| WO | WO 2018/078540 | 5/2018 | |
| WO | WO 2018/092059 | 5/2018 | |
| WO | WO 2018/092062 | 5/2018 | |
| WO | WO 2018/092063 | 5/2018 | |
| WO | WO 2018/092070 | 5/2018 | |
| WO | WO 2018/092071 | 5/2018 | |
| WO | WO 2018/130974 | 7/2018 | |
| WO | WO 2018/130976 | 7/2018 | |
| WO | WO 2018/130981 | 7/2018 | |
| WO | WO 2018/134747 | 7/2018 | |
| WO | WO 2018/146613 | 8/2018 | |
| WO | WO 2018/207128 | 11/2018 | |
| WO | WO 2019/034944 | 2/2019 | |
| WO | WO 2019/035023 | 2/2019 | |
| WO | WO 2019/111180 | 6/2019 | |

OTHER PUBLICATIONS

International Search Report and the Written Opinion dated Sep. 25, 2018 From the International Searching Authority Re. Application No. PCT/IB2018/050784. (18 Pages).

Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).

Boston Scientific "Rhythmia™ Mapping System: Rhythmia Disposables Product Information: Intellamap Orion™ High Resolution Mapping Catheter", Boston Scientific, 2 P., Sep. 2015.

Communication Relating to the Results of the Partial International Search dated Aug. 22, 2016 From the International Searching Authority Re. Application No. PCT/IB2016/052686.

Communication Relating to the Results of the Partial International Search dated Aug. 22, 2016 From the International Searching Authority Re. Application No. PCT/IB2016/052688.

Communication Relating to the Results of the Partial International Search dated Aug. 25, 2016 From the International Searching Authority Re. Application No. PCT/IB2016/052692.

Communication Relating to the Results of the Partial International Search dated Aug. 26, 2016 From the International Searching Authority Re. Application No. PCT/IB2016/052687.

International Preliminary Report on Patentability dated May 9, 2019 From the International Bureau of WIPO Re. Application No. PCT/IB2017/056616. (8 Pages).

International Preliminary Report on Patentability dated Nov. 23, 2017 From the International Bureau of WIPO Re. Application No. PCT/IB2016/052686. (11 Pages).

International Preliminary Report on Patentability dated Nov. 23, 2017 From the International Bureau of WIPO Re. Application No. PCT/IB2016/052687. (10 Pages).

International Preliminary Report on Patentability dated Nov. 23, 2017 From the International Bureau of WIPO Re. Application No. PCT/IB 2016/052688. (9 Pages).

International Preliminary Report on Patentability dated Nov. 23, 2017 From the International Bureau of WIPO Re. Application No. PCT/IB2016/052690. (9 Pages).

International Preliminary Report on Patentability dated Nov. 23, 2017 From the International Bureau of WIPO Re. Application No. PCT/IB2016/052692. (13 Pages).

International Preliminary Report on Patentability dated May 31, 2019 From the International Bureau of WIPO Re. Application No. PCT/IB2017/057186. (13 Pages).

International Search Report and the Written Opinion dated Feb. 1, 2018 From the International Searching Authority Re. Application No. PCT/IB2017/056616. (14 Pages).

International Search Report and the Written Opinion dated Jan. 2, 2019 From the International Searching Authority Re. Application No. PCT/IB2018/056158. (16 Pages).

International Search Report and the Written Opinion dated Jan. 3, 2017 From the International Searching Authority Re. Application No. PCT/IB2016/052688. (14 Pages).

International Search Report and the Written Opinion dated May 3, 2018 From the International Searching Authority Re. Application No. PCT/IB2017/057185. (18 Pages).

International Search Report and the Written Opinion dated Jun. 6, 2018 From the International Searching Authority Re. Application No. PCT/IB2018/050201. (24 Pages).

International Search Report and the Written Opinion dated May 9, 2018 From the International Searching Authority Re. Application No. PCT/IB2018/050192. (16 Pages).

(56) References Cited

OTHER PUBLICATIONS

International Search Report and the Written Opinion dated Oct. 12, 2016 From the International Searching Authority Re. Application No. PCT/IB2016/052686.
International Search Report and the Written Opinion dated Aug. 13, 2018 From the International Searching Authority Re. Application No. PCT/IB2018/053258. (15 Pages).
International Search Report and the Written Opinion dated Apr. 14, 2019 From the International Searching Authority Re. Application No. PCT/IB2018/059672. (49 Pages).
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Oct. 21, 2016 From the International Searching Authority Re. Application No. PCT/IB2016/052687. (16 Pages).
International Search Report and the Written Opinion dated Feb. 22, 2018 From the International Searching Authority Re. Application No. PCT/IB2017/057169. (14 Pages).
International Search Report and the Written Opinion dated Feb. 22, 2018 From the International Searching Authority Re. Application No. PCT/IB2017/057175. (15 Pages).
International Search Report and the Written Opinion dated Feb. 22, 2018 From the International Searching Authority Re. Application No. PCT/IB2017/057176. (15 Pages).
International Search Report and the Written Opinion dated Aug. 25, 2016 From the International Searching Authority Re. Application No. PCT/IB2016/052690.
International Search Report and the Written Opinion dated Apr. 30, 2018 From the International Searching Authority Re. Application No. PCT/IB2017/057186. (22 Pages).
International Search Report and the Written Opinion dated Apr. 30, 2018 From the International Searching Authority Re. Application No. PCT/IB2018/050195. (16 Pages).
International Search Report and the Written Opinion dated Nov. 30, 2018 From the International Searching Authority Re. Application No. PCT/IB2018/055344. (15 Pages).
Invitation to Pay Additional Fees and Communication Related to the Results of the Partial International Search and the Provisional Opinion dated Feb. 22, 2018 From the International Searching Authority Re. Application No. PCT/IB2017/057186. (12 Pages).
Invitation to Pay Additional Fees, Communication Relating to the Results of the Partial International Search and the Provisional Opinion dated Mar. 5, 2018 From the International Searching Authority Re. Application No. PCT/IB2017/057185. (13 Pages).
Invitation to Pay Additional Fees, Communication Relating to the Results of the Partial International Search and the Provisional Opinion dated Apr. 25, 2018 From the International Searching Authority Re. Application No. PCT/TB2018/050201. (14 Pages).
Notice Of Allowance dated Dec. 26, 2018 From the US Patent and Trademark Office Re. U.S. Appl. No. 15/572,815. (8 pages).
Official Action dated Aug. 30, 2018 From the US Patent and Trademark Office Re. U.S. Appl. No. 15/572,815. (22 pages).
Ahn et al. "Height-Based Deformation and Ray Supersampling for Colon Unfolding", ICAT06 Proceedings of the 16th international Conference on Advances in Artificial Reality and Tele-Existence, Lecture Notes in Computer Science, XP047402101, Hangzhou, China, Nov. 29-Dec. 1, 2006, p. 1098-1107, Nov. 29, 2006. Sections 3.1, 3.3, 5, Figs.2, 4, 5.
Anter et al. "Evaluation of a Novel High-Resolution Mapping Technology for Ablation of Recurrent Scar-Related Atrial Tachycardias," Heart Rhythm. 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.

Bartroli et al. "Nonlinear Virtual Colon Unfolding", Proceedings of the IEEE Conference on Visualization '01, VIS '01, XP031385694, San Diego, CA, USA, Oct. 21-26, 2001, p. 411-420, Oct. 21, 2001. Sections 4, 4.1, 4.2, 5.1, 7, Figs.1, 7a, 7b, 10.
Black-Maier et al. "Risk of Atrioesophageal Fistula Formation With Contact-Force Sensing Catheters", HeartRhythm. 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Canpolat et al. "Relationship Between Vitamin D Level and Left Atrial Fibrosis in Patients With Lone Paroxysmal Atrial Fibrillation Undergoing Cryoballoon-Based Catheter Ablation", Journal of Cardiology, 6991): 16-23, Published Online Aug. 21, 2016.
Caspi et al. "Modeling of Arrhythmogenic Right Ventricular Cardiomyopathy With Human Induced Pluripotent Stem Cells", Circulation: Cardiovscular Genetics, 6(6): 557-568, Published Online Nov. 7, 2013.
Cerit et al. "Association of Pre-Ablation Level of Vitamin D With Atrial Fibrillation Recurrence After Catheter Ablation", Europace, 19(9): 1586, Sep. 1, 2017.
Chierchia et al. "An Initial Clinical Experience With A Novel Microwave Radiometry Sensing Technology Used in irrigated RF Ablation for Flutter", Academic Hospital Brussels, Belgium, 1 P. Jan. 1, 2011.
Crospon "Esophageal Treatment by Esoflip®", Crospon, Product Sheet, 4 P., 2017.
Crospon "Flip® Technology", Crospon, Product Sheet, 6 P., 2017.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PV1 Lines to Incorporate Non-PV Targets fdentified by PreAblation Mapping with the AcQMap System: Update on the UNCOVER-AF Trial," EP Lab Digest, 17(5), May 2017, 5 pages.
Hilbert et al. "An Integrative Approach to Slow Pathway Modulation in AVNRT Using A Novel Ultra High-Density Electroanatomical Mapping System", Clinical Research in Cardiology. XP035518036, 104(8): 697-699, Published Online Mar. 31, 2015.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA. May 9-12, 2012, Session: Role of Autonomies in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III,# 3-53, May 10, 2012.
Jiang et al. "Association of Pre-Ablation Level of Potential Blood Markers With Atrial Fibrillation Recurrence After Catheter Ablation: A Meta-Analysis", Europace, 19(3): 392-400, Mar. 1, 2017.

(56) References Cited

OTHER PUBLICATIONS

Karim et al. "Surface Flattening of the Human Left Atrium and Proof-of-Concept Clinical Applications", Computerized Medical Imaging and Graphics, 38(4): 251-266, Jun. 2014.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
McDowell et al. "Virtual Electrophysiological Study of Atrial Fibrillation in Fibrotic Remodeling", Plos One, 10(2): e117110-1-e117110-16, Published Online Feb. 18, 2015.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Ranjan et al. "Gaps in the Ablation Line as A Potential Cause of Recovery From Electrical Isolation and Their Visualization Using MRI", Circulation: Arrhythmia and Electrophysiology, XP055452459, 4(3): 279-286, Published Online Apr. 14, 2011.
Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.
Shoemaker et al. "Common Genetic Variants and Response to Atrial Fibrillation Ablation", Circulation: Arrhythmia and Electrophysiology, 8(2): 296-302, Published Online Feb. 14, 2015.
St. Jude Medical "Cardiac Mapping System/ECG. NSite™ NavX™", St. Jude Medical, Products Sheet, 22 P., 2017.
Ueberham et al. "Genetic ACE I/D Polymorphism and Recurrence of Atrial Fibrillation After Catheter Ablation", Circulation: Arrhythmia and Electrophysiology, 6(4): 732-737, Published Online Jul. 22, 2013.
Vandekerckhove et al. "Flutter Ablation With an Irrigated Catheter Using Microwave Radiometry Sensing Technology: First Report in Men", Sint Jan Hospital, Department of Cardiology, Bruges, Belgium, 1 P., Jan. 1, 2011.
Wang et al. "Association of the Angiotensinogen M235T Polymorphism With Recurrence After Catheter Ablation of Acquired Atrial Fibrillation", Journal of the Renin-Angiotensin-Aldosterone System. 16(4): 888-897, Published Online Aug. 3, 2015.
Wang et al. "Colon Unraveling Based on Electrical Field: Recent Progress and Further Work", Proceedings of the SPIE 3660 Medical Imaging '99: Physiology and Function From Multidimensional Images, San Diego, CA, USA, Feb. 1999, XP055479173, 3660: 125-133, May 20, 1999. Abstract, Sections 1, 2.2, 2.3, Figs.2, 3.
Wang et al. "Microwave Radiometric Thermoetry and Its Potential Applicability to Ablative Therapy", Journal of Interventional Cardiac Electrophysiology, 4(1): 295-300, Feb. 2000.
Wittkampf et al. "LocaLisa: New Technique for Real-Time 3-Dimensional Localization of Regular Intracardiac Electrodes", Circulation, 99(10): 1312-1317, Mar. 16, 1999.
Zhong et al. "On the Accuracy of CartoMerge for Guiding Posterior Left Atrial Ablation in Man", Heart Rhythm, 4(5): 595-602, Published Online Feb. 9, 2007.
International Search Report and the Written Opinion dated Jun. 7, 2018 From the International Searching Authority Re. Application No. PCT/IB2018/050289. (16 Pages).

\* cited by examiner
† cited by third party

CHARACTERISTIC TRACK CATHETER NAVIGATION

RELATED APPLICATIONS

This application is a National Phase of PCT Patent Application No. PCT/IB2017/054263 having International filing date of Jul. 14, 2017, which claims the benefit of priority under 35 USC § 119(e) of U.S. Provisional Patent Application No. 62/362,146 filed on Jul. 14, 2016; and of U.S. Provisional Patent Application No. 62/449,055 filed on Jan. 22, 2017. The contents of the above applications are all incorporated herein by as if fully set forth herein in their entirety.

FIELD AND BACKGROUND OF THE INVENTION

The present invention, in some embodiments thereof, relates to the field of percutaneous catheter navigation and more particularly, to heart catheter navigation.

Systems and methods have been developed for non-fluoroscopic tracking of intra-body catheters, for example, for tracking a catheter during a cardiac procedure, such as intra-cardiac ablation.

Frederik H. M. Wittkampf, in U.S. Pat. No. 5,983,126 describes "A system and method are provided for catheter location mapping, and related procedures. Three substantially orthogonal alternating signals are applied through the patient, directed substantially toward the area of interest to be mapped, such as patient's heart. The currents are preferably constant current pulses, of a frequency and magnitude to avoid disruption with ECG recordings. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonal applied current signals. Three processing channels are used to separate out the three components as x, y and z signals, from which calculations are made for determination of the three-dimensional location of the catheter tip within the body."

SUMMARY OF THE INVENTION

There is provided, in accordance with some embodiments of the present disclosure, a method of associating intrabody catheter measurement values to positions within a body part, the method comprising: receiving a sequence of catheter-measured measurement values from at least one catheter moving along a measurement track within the body part; determining a transform establishing correspondence between the sequence of catheter-measured measurement values and a set of reference values; wherein the reference values are associated to positions along a predetermined reference track extending through a data representation of an anatomical space corresponding to the body part; and associating measurement values measured within the body part and away from the measurement track to positions in the data representation of the anatomical space, wherein the associating is based on: predetermined associations between reference values and positions within the data representation of the anatomical space, and the transform.

In some embodiments, catheter-measured measurement values comprise electrical field measurement values measured from a catheter electrode moving along a measurement track through electrical fields induced within the body part; and wherein the reference values comprise reference electrical field values.

In some embodiments, the set of reference electrical field values comprises one or more groups of reference electrical field values which indicate characteristic features of the induced electrical fields along the predetermined reference track.

In some embodiments, the catheter-measured electrical field measurement values comprise measured voltage values.

In some embodiments, the electrical fields induced within the body part comprise electrical fields induced from electrodes placed at intrabody positions.

In some embodiments, the intrabody positions comprise positions within the coronary sinus.

In some embodiments, the electrical fields induced within the body part comprise electrical fields induced from body surface electrodes.

In some embodiments, the set of reference values is provided as a sequence of reference values extending along the predetermined reference track.

In some embodiments, the transform is an affine transform. In some embodiments, the transform is a non-rigid transform. In some embodiments, the transform is determined based on a coherent point drift model of registration.

In some embodiments, the catheter-measured measurement values are measured along a track passing within a right atrium of a human heart; and the measurement values measured within the body part and away from the measurement track are measured within a left atrium of the human heart.

In some embodiments, the catheter-measured measurement values are measured along a track passing within a first blood vessel or heart chamber of a human; and the measurement values measured within the body part and away from the measurement track are measured within a second blood vessel or heart chamber of a human, different from the first.

In some embodiments, the previous measuring of the reference values was during a catheterization procedure, different from a catheterization procedure during which the measuring of the sequence of catheter-measured measurement values were received.

In some embodiments, the determining a transform comprises: comparing the sequence of catheter-measured measurement values to sets of reference values; and selecting one of the sets of reference values, based on the comparing.

In some embodiments, the method further comprises: determining the transform based on the selected set.

In some embodiments, the measurement values measured within the body part and away from the measurement track are measured within a lumen of a heart chamber comprising the measurement track.

In some embodiments, the measurement values measured within the body part and away from the measurement track are measured within a lumen of a heart chamber beyond the catheter from positions of the measurement track.

In some embodiments, the reference values are catheter-measured measurement values previously measured from at least one catheter.

In some embodiments, the previous measuring of the reference values was during a same catheterization procedure as the measuring of the received sequence of catheter-measured measurement values.

In some embodiments, the previous measuring of the reference values was during a different catheterization procedure as the measuring of the received sequence of catheter-measured measurement values.

In some embodiments, the previous measuring was in a different body part than the measuring of the received sequence of catheter-measured measurement values.

In some embodiments, the reference values are simulated measurement values simulated for positions within the data representation of the anatomical space.

In some embodiments, the simulated measurement values are simulated with respect to electrical fields induced within the anatomical space by simulated intrabody electrodes.

In some embodiments, the simulated measurement values are simulated electrical field measurement values simulated with respect to electrical fields induced within the anatomical space by simulated body surface electrodes.

In some embodiments, the electrical field measurement values measured within the body part and away from the measurement track are new measurements made after measurement along the measurement track.

In some embodiments, the associating uses electrical field measurement values obtained previously to the measurement along the measurement track.

In some embodiments, the reference values associated to positions within the data representation of the anatomical space comprise the previously obtained measurement values.

In some embodiments, the reference values are also associated to measurements of tissue state.

In some embodiments, the measurements of tissue state are measurements of tissue lesioning.

In some embodiments, the reference values are also associated to indications of previous ablation.

In some embodiments, the sequence of catheter-measured measurement values is measured from a plurality of crossing, time-varying electromagnetic fields.

In some embodiments, the method comprises updating the transform, based on further received catheter-measured measurement values.

In some embodiments, the method comprises iteratively re-performing the receiving, determining, and associating.

In some embodiments, the data representation of an anatomical space represents cardiovascular anatomy, and wherein the method comprises using the association of electrical field measurement values measured within the body part and away from the measurement track to positions in a data representation of the body part to guide navigation of the cardiovascular anatomy by the at least one catheter electrode.

There is provided, in accordance with some embodiments of the present disclosure, a system for associating measurement values to positions within a body part, the system comprising a processor, a data memory and a non-volatile instruction memory; wherein the instruction memory stores instructions which, when activated, operate the processor to: receive a sequence of catheter-measured measurement values from at least one catheter electrode moving along a measurement track within the body part; determine a transform establishing correspondence between the sequence of catheter-measured measurement values and a set of reference values; wherein the reference values are associated to positions along a predetermined reference track extending through a data representation of an anatomical space corresponding to the body part; and associate measurement values measured within the body part and away from the measurement track to positions in the data representation of the anatomical space, wherein the associating is based on: predetermined associations between reference values and positions within the data representation of the anatomical space, and the transform.

In some embodiments, catheter-measured measurement values comprise electrical field measurement values measured from a catheter electrode moving along a measurement track through electrical fields induced within the body part; and wherein the reference values comprise reference electrical field values.

There is provided, in accordance with some embodiments of the present disclosure, a method of associating intrabody catheter measurement values to positions within a body part, the method comprising: receiving a sequence of catheter-measured measurement values from at least one catheter moving along a measurement track within the body part; and determining a transform establishing correspondence between the sequence of catheter-measured measurement values and a set of reference values; wherein the reference values are associated to positions along a predetermined reference track extending through a data representation of an anatomical space corresponding to the body part.

In some embodiments, the associating is based on: predetermined associations between reference values and positions within the data representation of the anatomical space, and the transform.

There is provided, in accordance with some exemplary embodiments, a method of decreasing positional error of a mapping, wherein the mapping links intrabody electrical field parameter measurements to positions within a 3-D anatomical representation, the method comprising: defining at least one sequence of simulated electrical field parameter values corresponding to values along paths through one or more simulated electrical fields simulated within the 3-D anatomical representation; receiving a sequence of intrabody electrical field parameter measurements from at least one catheter electrode moving through one or more electrical fields induced within an anatomy, wherein the induced electrical fields and the anatomy are in respective correspondence with the simulated electrical fields and the 3-D anatomical representation; registering the sequence of electrical field parameter measurements to one of the sequences of simulated electrical field parameter values, wherein the registering includes accounting for the motion of the catheter electrode; and adjusting the mapping in a region of the 3-D anatomical representation away from the path of the sequence of simulated electrical field parameter values, based on the registering.

According to some embodiments, the registering comprises defining a calculated transform mapping between the sequence of electrical field parameter measurements and the one of the sequences of simulated electrical field parameter values; and wherein the adjusting uses the calculated transform.

According to some embodiments, the calculated transform is an affine transform.

According to some embodiments, the sequence of electrical field parameter measurements is performed along a track passing within a right atrium of a human heart; and the region of the 3-D anatomical representation away from the path of the sequence of simulated electrical field parameter comprises a left atrium of the human heart.

According to some embodiments, the registering comprises: comparing the sequence of intrabody electrical field parameter measurements to two or more sequences of simulated electrical field parameter values; and selecting the one of the sequences of simulated electrical field parameter values using in the registering, based on the comparing.

According to some embodiments, the comparing is based on the calculated transform.

According to some embodiments, the registering is based on similar identified features between the sequence of electrical field parameter measurements and the one of the sequences of simulated electrical field parameter values.

According to some embodiments, the similar identified features comprise at least one of a starting point and an ending point.

According to some embodiments, the similar identified features comprise similar electrical field parameter changes occurring over a length of between 5 mm and 5 cm.

According to some embodiments, the similar electrical field parameter changes are determined by isolating high spatial frequency components of the electrical field parameter changes.

According to some embodiments, the 3-D anatomical representation represents cardiovascular anatomy, and comprising using the adjusted mapping to guide navigation of the cardiovascular anatomy.

According to some embodiments, the method comprises iteratively re-performing the moving, receiving, registering, and adjusting.

According to some embodiments, the simulated electrical field parameter values are simulated for a plurality of crossing, time-varying electrical fields.

According to some embodiments, the sequence of electrical field parameter measurements is measured from a plurality of crossing, time-varying electrical fields.

According to some embodiments, the 3-D anatomical representation comprises 3-D image data of the represented anatomy.

According to some embodiments, the electrical field parameter values and measurements comprise voltages.

According to some embodiments, the mapping comprises the simulated electrical field parameter values and their positions within the 3-D anatomical representation; and wherein the mapping is applied by corresponding the electrical field parameter measurements to the simulated electrical field parameter values.

There is provided, in accordance with some exemplary embodiments, a system for decreasing positional error of a mapping, wherein the mapping links intrabody electrical field parameter measurements to positions within a 3-D anatomical representation, the system comprising: an electrical field simulator, comprising computer circuitry configured to calculate intrabody electrical field parameter values of one or more simulated intrabody electrical fields, simulated within the 3-D anatomical representation; and a position analyzer, comprising computer circuitry configured to: define at least one sequence of simulated electrical field parameter values corresponding to values along intrabody paths through the one or more simulated electrical fields; receive a sequence of intrabody electrical field parameter measurements from at least one catheter electrode moving through one or more electrical fields induced within an anatomy, wherein the induced electrical fields and the anatomy are in respective correspondence with the simulated electrical fields and the 3-D anatomical image data; register the sequence of electrical field parameter measurements to one of the sequences of simulated electrical field parameter values, wherein the registration includes accounting for the motion of the catheter electrode; and adjust the mapping in a region of the 3-D anatomical representation away from the path of the sequence of simulated electrical field parameter values, based on the registration.

According to some embodiments, the position analyzer is further configured to: determine a calculated transform transforming between the sequence of electrical field parameter measurements and the one of the plurality of sequences of simulated electrical field parameter values; and register the sequence of electrical field parameter measurements to the one of the plurality of sequences of simulated electrical field parameter values based on the calculated transform.

There is provided, in accordance with some exemplary embodiments, a method of decreasing positional error of an electrical field parameter simulation, wherein the simulation maps positions within a 3-D image representing an individual cardiovascular anatomy to intrabody electrical field parameter values predicted thereat, the method comprising: defining for each of a plurality of lumenal regions of a reference cardiovascular anatomy an associated characteristic feature of electrical field parameter measurements experienced by a catheter electrode moving along the lumenal region and through a reference electrical field; measuring a sequence of intrabody electrical field parameter measurements from at least one catheter electrode while the catheter electrode moves along a track constrained by the individual cardiovascular anatomy and through an electrical field imposed across the individual cardiovascular anatomy from body surface electrodes; and registering the positions of the sequence of intrabody electrical field parameter measurements to the 3-D image, based on matching of the sequence of intrabody electrical field parameter measurements to at least one of the associated characteristic features; and adjusting the electrical field parameter simulation, based on the registering.

According to some embodiments, the adjusting comprises applying the calculated transform to adjust the expected intrabody electrical field parameter measurements and expected electrical field parameter values; wherein the adjusting comprises applying the calculated transform to adjust the expected intrabody electrical field parameter values.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electrical, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
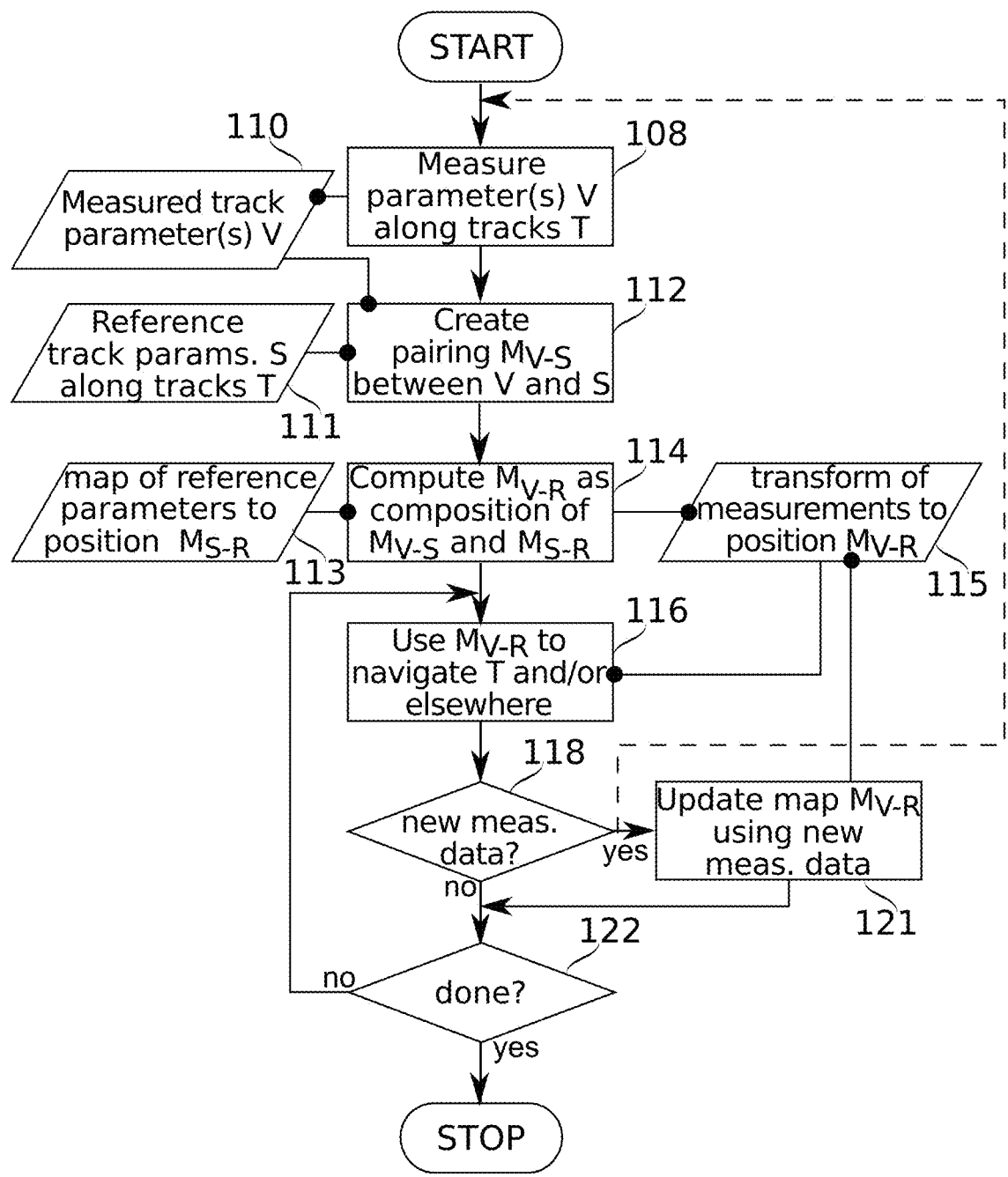
FIG. 1A is a flowchart schematically representing a method for registration of electrical field measurements measured along tracks of catheter motion to reference electrical field parameter values associated with positions in a data representation of an anatomical space, and use of a transform produced during the registration to associate further intrabody electrical field measurements to intrabody positions, according to some embodiments of the present disclosure.

The present invention, in some embodiments thereof, relates to the field of percutaneous catheter navigation and more particularly, to heart catheter navigation.

Overview

A broad aspect of some embodiments of the invention relates to the assignment of spatial positions to measurements of intrabody, catheter-measured parameters. In some embodiments, the catheter-measured parameters are measurements of one or more electrical fields. Intrabody measurements of electrical fields are used herein as an example; however, it should be understood that optionally intrabody measurements are additional or alternatively of another parameter, for example DC, pulsed DC and/or AC magnetic field properties, acoustic properties (e.g., related to ultrasound wavelengths), and/or optical properties.

The assignment is optionally used in the intrabody navigation of the catheter to and/or within a target site: for example, to make measurements of tissue state and/or function, and/or to provide a treatment such as tissue ablation and/or inactivation to block impulses leading to atrial fibrillation. Optionally, the assignment is used in reconstruction of the shape of a target site using measurements of electrical field parameters. Herein, examples are provided in terms of cardiovascular body parts, and in particular the heart and vasculature of the heart. However, it should be understood that in some embodiments of the invention, the same principles are optionally applied, changed as necessary, to catheter and/or other endolumenal device movements in other body parts, for example, in the brain, kidneys, and/or digestive tract.

In some embodiments, intrabody navigation of a catheter is based on measurements by a catheter-borne sensor (e.g., an arrangement of one or more electrodes) of one or more electrical fields induced through a region of a patient's body. For use in navigation and/or reconstruction, the measurements are mapped to (i.e., assigned to and/or associated with) probe locations and/or probe orientations in space.

In some embodiments, electrical field mapping to intrabody locations is at least partially based on a pre-existing mapping of electrical field parameter values to positions. In some embodiments, the pre-existing mapping comprises an electrical field simulation using tissue-dependent differences in dielectric properties to predict electrical field properties (for example, voltage, impedance, and/or dielectric properties) at different intrabody locations. In some embodiments, the pre-existing mapping to intrabody location comprises a set of previous measurements already assigned to positions: for example, measurements obtained during a previous procedure in the same and/or one or more other patients; and/or measurements earlier obtained from a current patient during a current procedure. Differences in spatial position mapping from simulated and/or previously obtained and currently measured electrical field parameters may arise; due, for example: to variation in the impedance of actual electrodes from those used previously and/or the simulation, to changes or undetermined variables in a state of the patient anatomy (e.g., a state of hydration), and/or to differences between the actual anatomy of the patient and the model used in simulation and/or anatomy of another patient. Also indicated in the figures are positions of the mitral valve aperture 275, and the left atrial appendage 273. These features may also be used additionally and/or alternatively as landmarks for pre-determined tracks.

An aspect of some embodiments of the invention relates to the registration (optionally comprising refinement of registration) of catheter-sensed intrabody voltage field parameter values, measured along a track defined in a cardiovascular anatomy to pre-existing reference electrical field parameter values ("reference electrical field parameter values" provide a particular example of what is also referred to herein more generally as "reference values"), wherein the reference values are themselves associated with positions along a track in a data representation of a reference anatomical space. Optionally, an electrical field parameter used comprises, for example: voltage, impedance, electrical current, and/or any other parameter characterizing an electrical field. The reference values may be ordered in a sequence. By "sequence" is meant that that voltage field parameter values are ordered: for example, ordered in time, and/or along a distal/proximal axis of an actual and/or virtual catheter. Optionally, the order of a sequence is also associated with an indication of distance (e.g., of catheter advance/pullback) and/or interval (e.g., sampling rate).

The reference anatomical space (also referred to herein as anatomical space) may correspond to the body part and/or cardiovascular anatomy. For example, the data representation of the anatomical space may be a data representation of the very same cardiovascular anatomy. The representation may be, for example, image data obtained earlier; e.g., in a preceding procedure, or earlier in the present procedure. In other examples, the data representation may be of a cardiovascular anatomy of a different patient, or taken from an atlas representing a "typical" cardiovascular anatomy. The "typical" cardiovascular anatomy may be typical to a reference group, for example, people of common gender, age group, body weight range, etc.

The track in the cardiovascular anatomy is referred to herewith as measurement track, and the track in the data representation is referred to herein as reference track. Optionally, the measurement track is defined by lumens in the cardiovascular anatomy. In some embodiments, the measurement track is defined between two landmarks in the cardiovascular anatomy and including the region in between; e.g., between the fossa ovalis and a pulmonary vein. The reference track may be defined between representations of two landmarks that correspond to the landmarks between which the measurement track is defined. Similarly, the reference track may be defined by a data representation of a lumen (e.g., an extent of blood vessel) corresponding to a lumen defining the measurement track.

The registration, in some embodiments, is characterized by a transform produced by the registration process. The transform may assign positions along the reference track to electrical field parameter values measured along the measurement track. In some embodiments, the transform is used to assign positions to new electrical field measurement values, measured at positions away from the measurement track. The assignment of positions to measurements taken away from the measurement track may be based on pre-existing reference mapping of electrical field parameter values to positions away from the reference track.

The reference sequence optionally comprises simulated and/or previously measured electrical field parameter value data. The data representation of the reference anatomical space optionally comprises 3-D imaging data (for example, CT and/or MRI data). Optionally or additionally, the data representation of the reference anatomical space comprises a spatial reconstruction of the anatomical space based on any suitable non-imaging data, for example, previous measurements of electrical field parameter values. The reference sequence optionally comprises electrical field values associated with corresponding positions in the anatomical space. For example, if a simulation based on CT image showed that at a certain position in the reference track the electrical field parameter has a certain value, the reference sequence may associate the certain value with the certain position. Similarly, if in a preceding procedure (or at an earlier stage of the present procedure) a measured value of an electrical field parameter was associated with a certain position in a reconstruction of the anatomical space, the reference sequence may associate the measured value with the certain position.

In some embodiments of the invention, registration of a reference track to a measurement track comprises comparing the measurement track to each of a plurality of reference tracks.

Optionally, the comparing includes selection of particular reference tracks matching measurement tracks from among a plurality of available, pre-defined reference tracks. The selection is based, for example, on feature similarities to the measurement track, on user selection, and/or on the following of a specified protocol for track measurement. For example, a user may indicate through a user interface which pre-defined track is being followed, a user interface may direct a user to follow a particular pre-defined path, and/or a currently measured track is matched to a pre-defined reference track according to their similarity and/or by ruling out other candidate reference tracks based on insufficient similarity.

Then, in some embodiments, measurements of electrical field parameter values of the measurement track are registered to positions associated with the reference track.

In some embodiments, the reference tracks make part of the reference space, which is a data representation of an intrabody region larger than the reference track. Optionally, registration of a measurement track to a reference track yields a transform which applies with useful accuracy throughout a larger part of the reference space to which the reference track belongs. In some embodiments, a plurality of track pairs (that is, track pairs covering at least partially different regions of the reference space) are registered to yield a transform. In this context, a track pair is a measurement track paired with the corresponding reference track. In some embodiments, a single transform is found to register each of the measurement tracks to its corresponding reference track.

In some embodiments, a long pullback provides a long base along which a transform can be estimated, potentially allowing averaging to reduce sensitivity to measurement errors and/or localized distortions in the reference data. As used herein, "pullback" refers to a movement of the catheter along a blood vessel or other body conduit back from the current position towards the region where the body conduit was entered by the catheter head.

In some embodiments, definition of a reference track begins from a general anatomical specification of regions which may be visited by a catheter along the track. Optionally, the specification is of regions that are normally traversed by a physician in the course of a procedure, for example, blood vessels and/or other body lumens that are traversed by a catheter en route to a target region. The specification may be based, for example, on regions that can be easily identified upon entry during catheter operation, regions that can be reliably and/or easily entered during catheter operation, and/or regions that have particular significance for a procedure. These regions may be considered as landmarks used to broadly define the track, though they do not necessarily encompass the totality of the track. Once defined, tracks may also comprise intermediate positions between landmarks which are also informative to the process of registration. Several examples of tracks related to navigation of a cardiovascular space are described, for example, in relation to FIGS. 2A-2C herein.

Due to the elongate structure of catheters, regions along a track are initially reached in a particular proximal-to-distal order, while during pullback (retraction of the catheter) they are navigated in a distal-to-proximal order. Proximal-to-distal navigation is prone to delays and trial-and-error, as the catheter is operated to seek its next target. Pullback navigation is potentially more reproducible, since it occurs along a course which the position of the catheter has already determined.

Continuing the discussion of how reference tracks may be pre-defined: given a general anatomical specification of regions which may be visited by a catheter along the track, electrical field parameter values and their associated positions falling along a pre-determined reference track are optionally be selected in one of at least two different ways. One way is to define a virtual path through a data representation of an anatomical space, wherein the virtual path links visited regions along lumens which a catheter could be passed along. Positions along the virtual path are associated with corresponding electrical field measurement values, and ordered along the path. The sampling density used may be at least, for example, about every 1 mm, 2 mm, 5 mm, 10 mm, or at another higher, lower, or intermediate measurement density. This method may be used, for example, to create pre-defined tracks based on simulation data. This method may also be used to create pre-defined tracks based on actual prior measurements; wherein positions existing along the track were previously measured, while optionally ignoring the sequencing of positions taken during the actual prior measurements. Another method is to use prior measurements in their original sequence—that is, the order in which measurements were taken—essentially, measurements made along a previously recorded instance of a catheter moving along the track. The sampling density used may be at least, for example, about every 1 mm, 2 mm, 5 mm, 10 mm, or at another higher, lower, or intermediate measurement density. Additionally or alternatively, values may be measured as the catheter moves, at a sampling rate (optionally fixed) of about 10 Hz, 50 Hz, 100 Hz, or another higher, lower, or intermediate sampling rate.

In some embodiments, a transform model at least potentially comprising a large number of parameters is used. The transform may be, for example, a non-linear, and optionally non-affine transform such as a non-rigid coherent point drift-based transform. For example, transform parameters may be assigned to adjust to local non-linearities at any suitable feature scale, for example, 5 mm, 10 mm, 15 mm, 20 mm, 30 mm, 50 mm, or another scale. Optionally, registration of several different measurement tracks to a plurality of reference tracks may be used to supply information to help evaluate parameter values that provides a best fit over all the tracks. In some embodiments, the plurality of tracks are selected to set the extremities of an anatomical region of interest, for example by visiting particular landmarks that have a non-degenerate distribution (that is, "3-D", not all co-linear and/or co-planar) around an anatomical region of interest. Moreover, local non-linearities in the track-to-track registration may be treated as indicating (e.g., after suitable interpolation) transform non-linearities which also extend outside the registration track itself.

Even though sampling just a few tracks may in principle fail to sample local features falling between tracks, interpolation and/or extremity sampling potentially constrains error to within limits that are consistent with requirements for accuracy of navigation and/or overall anatomical shape reconstruction. In some embodiments, the registration of the tracks may be used for providing an initial mapping, and when further measured values are collected, the mapping is improved to include these values. This way, the tracks may enable generating an image almost immediately (as traversing the tracks takes very short time), and this image may be improved when the procedure continues. In the present disclosure and claims, the word "traverse" and its inflections mean to go or travel across, along, and/or through.

Accordingly, in some embodiments, a transform (affine or non-affine) which adjusts to register reference and (newly) measured tracks is applied to regions away from the track-traversed regions. For example, registration adjustments comprising scaling, offset, rotation and/or shear along the track are optionally propagated throughout a larger region of the simulation. Similarly, in a non-rigid CPD-based transform, the same rule for drifting points from measurement track to reference track may apply also for drifting points from measurement space—outside the tracks—to reference space. Optionally, registration adjustments by the transform also allow for non-affine transformations (e.g., relative shrinking and/or expanding certain sub-regions of the reference space in order to get an optimal fit).

Potentially, the method overall allows measurements from along a few well-defined track pullbacks and/or other catheter movements to quickly refine the accuracy with which electrical field parameter values in a navigation space are assigned a spatial distribution.

For example, in some embodiments, transformation of a simulated electrical field to match measured voltages is potentially accomplished for a left atrium before the left atrium is actually visited. Depending on the method of approach to the heart, the registration is optionally achieved, for example, based on traversals of regions that happen to lie on the way of the catheter to its destination, and/or are visited by the catheter before the catheter reaches its destination. For example, if the catheter visits the right atrium on its way to the left atrium, a transform useful in registering measurements taken within the left atrium may be generated based on readings taken in the right atrium, before the left atrium is visited. Similarly, a transform useful in registering measurements taken within the left atrium may be generated based on readings taken in the aorta. Another waypoint optionally visited and used in registration is the right ventricle/pulmonary artery confluence. By reducing time and/or effort spent on preliminary acquiring of navigation reference data, there is potentially provided increased speed and/or effectiveness of the catheterization procedure overall.

In another example, there may exist for a patient a left atrium reconstruction from a previous procedure in which induced electrical field voltages (an example of a type of electrical field parameter value) were assigned to spatial positions within the left atrium. In a new procedure, the electrical fields may be induced from electrodes having somewhat different placements and/or properties. Optionally or additionally, the induced fields may differ because the patient's own anatomy has changed: e.g., due to changes in hydration, weight, disease state, and/or another parameter. In some embodiments, the old left atrium reconstruction data is put to use in a new procedure by registration with a plurality of measurement tracks that traverse paths corresponding to pre-determined tracks through the old mapping. Once the new tracks are aligned with the old tracks, the rest of the old data is also registered, by suitable application of the transform that achieves the new-to-old track alignment. Optionally, the reference map is not from an old procedure in the same patient, but rather an old procedure in a different patient (or a combination of a plurality of patients); for example, an atlas map.

In another example, an electrical field configuration may change during a procedure. In some embodiments, one or more electrode catheters are placed at an intrabody position (such as the coronary sinus) in order to generate reference electrical fields for use in positioning. Use of such intrabody-generated electrical fields for mapping and/or navigation is described in U.S. Provisional Patent Application No. 62/449,055 filed Jan. 22, 2017; the contents of which are incorporated herein by reference in their entirety.

For a variety of reasons, there may be a gradual drift or sudden displacement of the intrabody electrode and/or its electrical properties, introducing an electrical field disruption such that new measurements made from a same intrabody position (e.g., by another, measuring electrode catheter) do not directly match previous measurements. Additionally or alternatively, if body surface electrodes are used, there may also be drifting or events which disrupt electrical field configuration.

However, the disruption does not necessarily result in mere scrambling. Rather, the disruption may be sufficiently systematic that re-registration can be performed along one or a plurality of tracks (e.g., 1-5 tracks), substantially as described for the case of data from an older procedure, an atlas map, and/or a simulation. A potential advantage of this is to allow a more rapid recovery from disruption/drift, by using a relative small amount of new measurement data to restore usefulness to a larger body of measurement data already recorded.

An aspect of some embodiments of the invention relates to the registration of catheter-sensed intrabody voltage field measurements along tracks to characteristic feature-defined tracks of voltage field measurements. A characteristic feature-defined track is defined by one or more characteristic features defined by a group and/or sequence of values which indicate the presence and/or position of an identifiable feature. By identifiable feature should be understood a feature which is identifiable in common across different patient anatomies and/or procedures by some characteristic of its structure, examples of which are given in further definitions and examples described herein. Herein, such characteristic feature-defined tracks are also referred to as "characteristic feature paths" or "characteristic feature tracks".

A "characteristic track" more broadly (embodied as either a measured track or a reference track) may be based on one or both of at least one characteristic feature, and a relatively continuous sequence of values (which may or may not be themselves also comprise a characteristic feature). By "relatively continuous" sequence of values should be understood one or more of the following: a continuously sampled sequence of values compared to the track length (e.g., at least 100 samples obtained along the track without gaps of more than 5 mm over a track of at least 3 cm, 5 cm, 7 cm, 10 cm, or another distance; and/or samples obtained at least 10 Hz during movement along a track); optionally the sequence of values is defined along a path linking two or more anatomically salient landmarks; and In some embodiments, electrical field measurements undergo characteristic change as a catheter is navigated along a certain standard path (these measurements together optionally form a group defining a characteristic feature), wherein the characteristic change itself identifies (as a characteristic feature) the position of the catheter in the anatomy. For example, a catheter pull-back through the aorta (e.g., aortic valve to ascending aorta, thence through the transverse arch and thoracic aorta, and terminating in the abdominal aorta) will generally define a "walking stick"-shaped path (reflected in measured voltages as well) in a predefined intra-thoracic plane. A reversing pattern of voltage change through the upper arc of the walking stick "handle" optionally is used to identify the track as being in the aortic arch, and/or to locate it relative to a geometrical representation of aortic arch anatomy. In another example, a right-sided pullback from the superior vena cava through the right atrium and into the inferior vena cava will be a typical straight line through a long distance with minimal angulation. The length is optionally itself identifying. Additionally or alternatively, registration along the path is performed, for example, with reference to the registration parameters of another track (e.g, making use of a well-defined place where the other track branches from the current path). Also additionally or alternatively, registration may be based on electrical field features along the current track, even if the geometry itself is ambiguous. For example, there may be distinct electrical field features even along a geometrically straight track, since the electrical field may be non-uniformly changing as a function of position.

Characteristic feature-defined tracks defined by major anatomical features are potentially substantially independent of influences due to different mapping styles and/or other inter-user variability. Optionally, the definition of the characteristic feature-defined track is modified a generic (e.g., across patient) definition to account for the anatomy of the patient, e.g., as known from imaging data and/or previous mapping procedures. Additionally or alternatively, features of the characteristic feature-defined track may be defined relative to common anatomical landmarks.

Optionally, the definition of a characteristic feature-defined track is also based on the choice of a point of entry and/or the catheter mechanics of the particular tool used.

In some embodiments, a characteristic feature-defined track is sufficiently stereotyped that it is identifying, optionally without explicit comparison to a simulation or other pre-existing reference space. For example, a characteristic curvature (like that described for the aortic arch) is optionally used as a basis for selection of a track from among a plurality of candidate tracks to which measurements of electrical fields are to be registered. In some instances, the characteristic may make a particular reference track identifiable because it doesn't occur in any other pre-defined reference track.

In some embodiments, determination of catheter position is based on detecting characteristic electrical field features as a function of catheter movement: that is, not just by comparison to the feature in isolation, but also using an "expectation" of position based on where and/or how far the catheter has moved already. For example, there may be two positions that have a similar feature in common, but only one of them is expected to be next accessible to the catheter—and that is the position assigned, in some embodiments, once the feature is indeed encountered. Accordingly, the determination produces a position estimate based on where, anatomically, the characteristic electrical field features are expected. Optionally, the position estimate also includes consideration of the rate and/or amount of catheter advance and/or retraction (pullback).

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Methods of Simulated Voltage Registration

Reference is now made to FIG. 1A, which is a flowchart schematically representing a method for registration of electrical field measurement values measured along tracks of catheter motion to reference electrical field parameter values associated with positions in a data representation of an anatomical space, and use of a transform produced during the registration to associate further intrabody electrical field measurements to intrabody positions, according to some embodiments of the present disclosure.

At block 108, in some embodiments, one or more sequences of voltages V are measured along at least one member $T_i$ of a corresponding set of catheter tracks T.

Herein, "voltage" is discussed as an example of an electrical field parameter for which values may be measured and/or simulated. It should be understood that other electrical field parameters (and/or measurable properties of a tissue environment indicated by electrical field measurement) may be substituted for voltage: for example, impedance measurements and/or dielectric property measurements. Electrical field measurements may comprise a plurality of measurements at any given position, optionally treated as a position-indicating unit. For example, crossed, oscillating electrical fields are induced intra-body in some embodiments in such a way that changes in measurements of fields oscillating at different frequencies associate with different directions ("axes", though not necessarily orthogonal axes) of catheter probe displacement. The electrical fields are optionally induced intrabody from body surface electrodes, and/or by electrodes positioned within the body.

In some embodiments, an individual catheter track $T_i$ is defined as a course along which a substantially monotonic (one-directional) advance or pullback movement of a catheter 9 occurs. The catheter movement moves a catheter probe 11 carrying one or more electrodes 3 which are used in voltage sampling. Catheter 9, catheter probe 11, catheter electrodes 3 and other system components are described, for example, in relation to FIG. 4.

A monotonic movement is potentially most useful because characteristics tracks may be more easily defined, executed and/or identified as one-directional movements than as reversing movements. A potential advantage of using catheter pullback tracks in particular is that it is relatively reliable to achieve a rapid, smooth pullback motion along a track compared to advancing of a catheter. For example, a first landmark may be located using the catheter, and the catheter then advanced distally to a second landmark. Positioning at the second landmark may involve hunting and/or trial and error. On the pullback, however, the catheter naturally proceeds between the two landmarks through a characteristic path governed by anatomy and/or the mechanical properties (e.g., flexibility) of the catheter itself, since more proximal portions of the catheter act to guide the movement of more distal portions.

In some embodiments, catheter pullback/advance distance is automatically measured in tandem with voltage measurements (e.g., by use of a motion encoding sensor configured to detect sliding motions of the catheter), to allow distance-voltage pairs to be directly assigned. In some embodiments, catheter movement is executed by a doctor with sufficient swiftness and/or consistency that a substantially constant speed throughout at least most of the catheter track can be assumed in registration. In some embodiments, catheter speed is treated as an unknown variable which is adjustable as part of finding a best fit (minimized error fit) to an acceleration/deceleration model, for example as described in relation to block 112, and/or in relation to FIGS. 3A-3B.

Optionally, a track is at least partially predefined as a "characteristic" track. A characteristic track (or characteristic-defined track) is a track defined according to landmarks which are generally available from patient to patient, and can be traversed consistently by users having different catheter handling techniques while remaining identifiable from electrical field measurements. Optionally, a characteristic track is described in terms of anatomical landmarks. For example, a track may be defined as a course running along and/or between one or more anatomical landmarks such as blood vessels, heart chamber structures, and the like. Additionally or alternatively, the definition of a track may at least partially be in terms of spatial coordinates (for example, defined from spatial coordinates of imaging data such as MRI or CT) and/or distance measurements (e.g., along a blood vessel). Additionally or alternatively, the definition of a track is at least partially expressed in terms of voltages and/or other electrical field measurements (for example, simulated voltages along tracks of spatial coordinates), and/or features of voltage sequences (e.g., first or greater-order derivatives, zero-crossings, and/or inflection points). In some embodiments, another electrical field property (optionally, a property modulated by local tissue properties) is measured, for example, impedance and/or dielectric properties. In some embodiments, tracks are identified based features resulting from non-uniformity of the electrical fields imposed for navigation, such as relative compression and/or expansion of iso-voltage contour distances. The non-uniformity of the electrical fields may result, for example due to the fields being transmitted through nonlinear and/or non-isotropic media (e.g., body tissue). In some embodiments, such non-uniformities are used as part of a characteristic track's identification. For example, regions deep inside the pulmonary veins typically show a relatively higher impedance, which is optionally used as a part of a characteristic track definition. Some examples of characteristic tracks are described in relation to FIGS. 2A-2B, herein. Optionally, a characteristic track is only partially defined along a catheter movement path (for example, at a plurality of discrete landmark sites). Regions in between are optionally handled by interpolation, for example, linear interpolation, or another type of interpolation.

In some embodiments, catheter tracks usable as part of the set of catheter tracks T are predetermined and/or preselected, e.g., according to the members of a set of reference tracks T for which electrical field parameter values S are available (block 111), or a selected (automatically and/or by a user) subset thereof. Additionally or alternatively, movements of the catheter are automatically assessed, and those movements having properties identifiable as useable tracks are automatically identified and/or used as tracks of catheter tracks T. An example of a property of a track that makes the track suitable for automatic identification is that the track comprises a sufficient distance of one-directional catheter pullback or advance. In some embodiments, a catheter track is identified automatically as corresponding to some pre-defined track definition. Optionally, a user identifies at least the general course of a catheter track (e.g., via a user interface by selecting a named predefined track from a menu) before, during, or after execution of a movement along a track. Optionally, a user interface prompts a user to move through a particular track. Optionally, the user indicates when the track is started and/or ended. Optionally, track starting/ending is identified automatically based on properties of the catheter movement (e.g., landmark identification, and/or initiation/cessation of changes in measured electrical field properties)

Figure 1B:
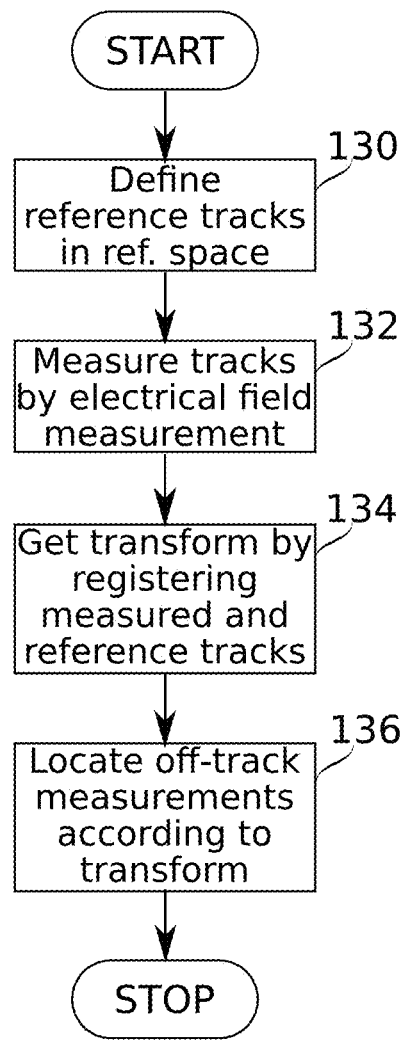
FIG. 1B is a schematic flowchart of a method of assigning measured intrabody electrical field parameter values to positions within a cardiovascular anatomy, according to some exemplary embodiments of the present disclosure.
Figure 1C:
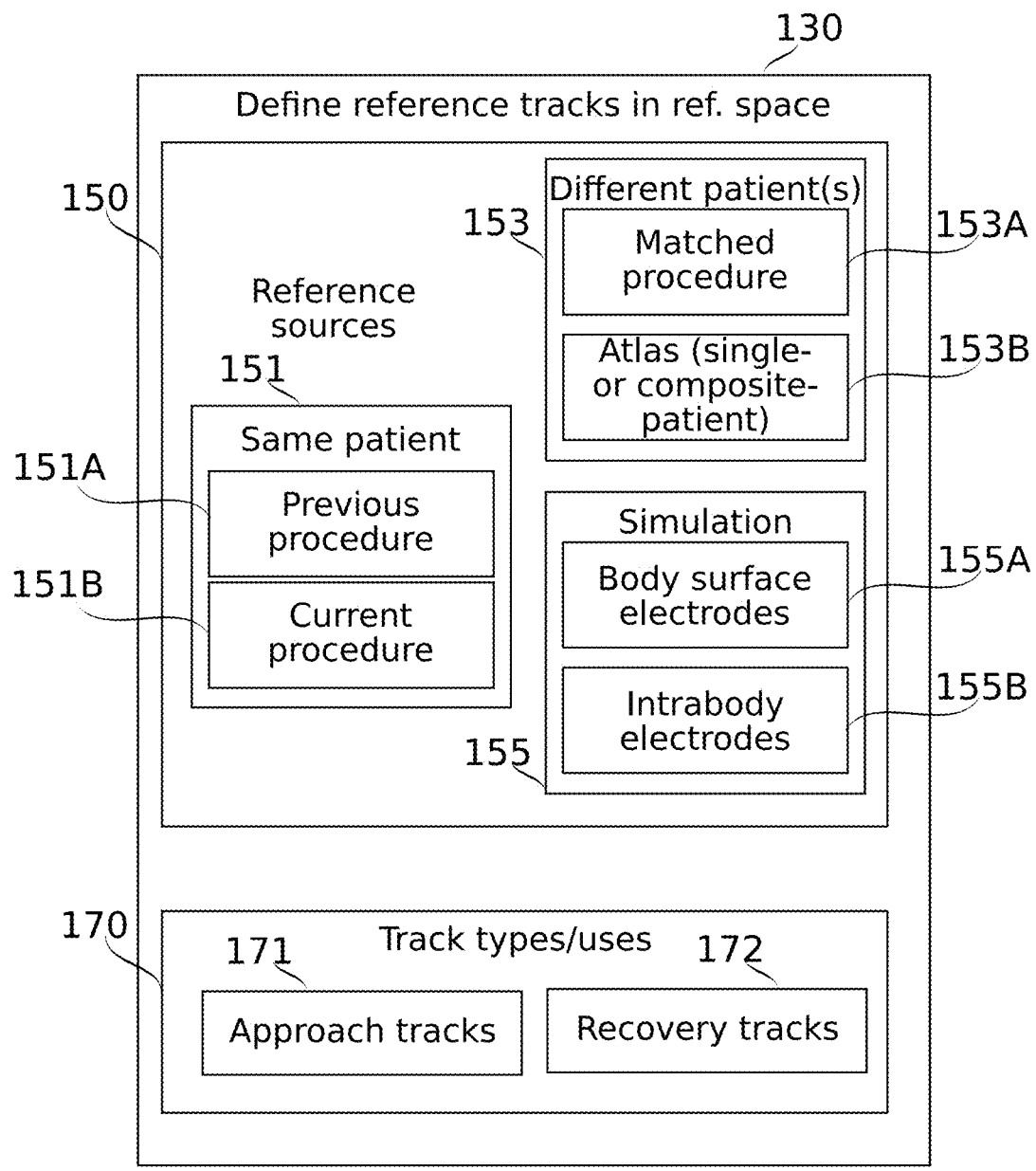
FIG. 1C is a schematic representation of aspects of block 130 of FIG. 1B, according to some embodiments of the present disclosure.

Electrical field parameter values along tracks $T_1, T_2 \ldots T_n$ are optionally measured in a concerted sequence (for example, two, three, or more tracks measured before moving on to the execution of other blocks of the flowchart of FIG. 1C), and/or iteratively (for example, in a loop passing through the main operational blocks of the flowchart and then back to block 108 as indicated by the optional fly-back arrow connecting decision block 118 to block 108).

The set of measured track voltage sequences V (one track voltage sequence $V_i$ for each measured track $T_i$) is optionally stored as measured track voltages V indicated at data structure block (rhomboid) 110.

At block 112, in some embodiments, a set of reference track electrical field parameter values S (stored, for example, at data structure block 111) is received. The reference track may comprise, for example: a track in a simulated reference space, a track in a reference space defined during a previous procedure in the same or a different subject, or a track in a reference space defined during a current procedure.

Also received at block 112 are track voltages V of block 110. Matching members of S and V are then paired based on their homologous features, and mapping furthermore applied so that corresponding regions of each matching pair $S_i, V_i$ are related through a mapping $M_{V-S}$.

Figure 4:
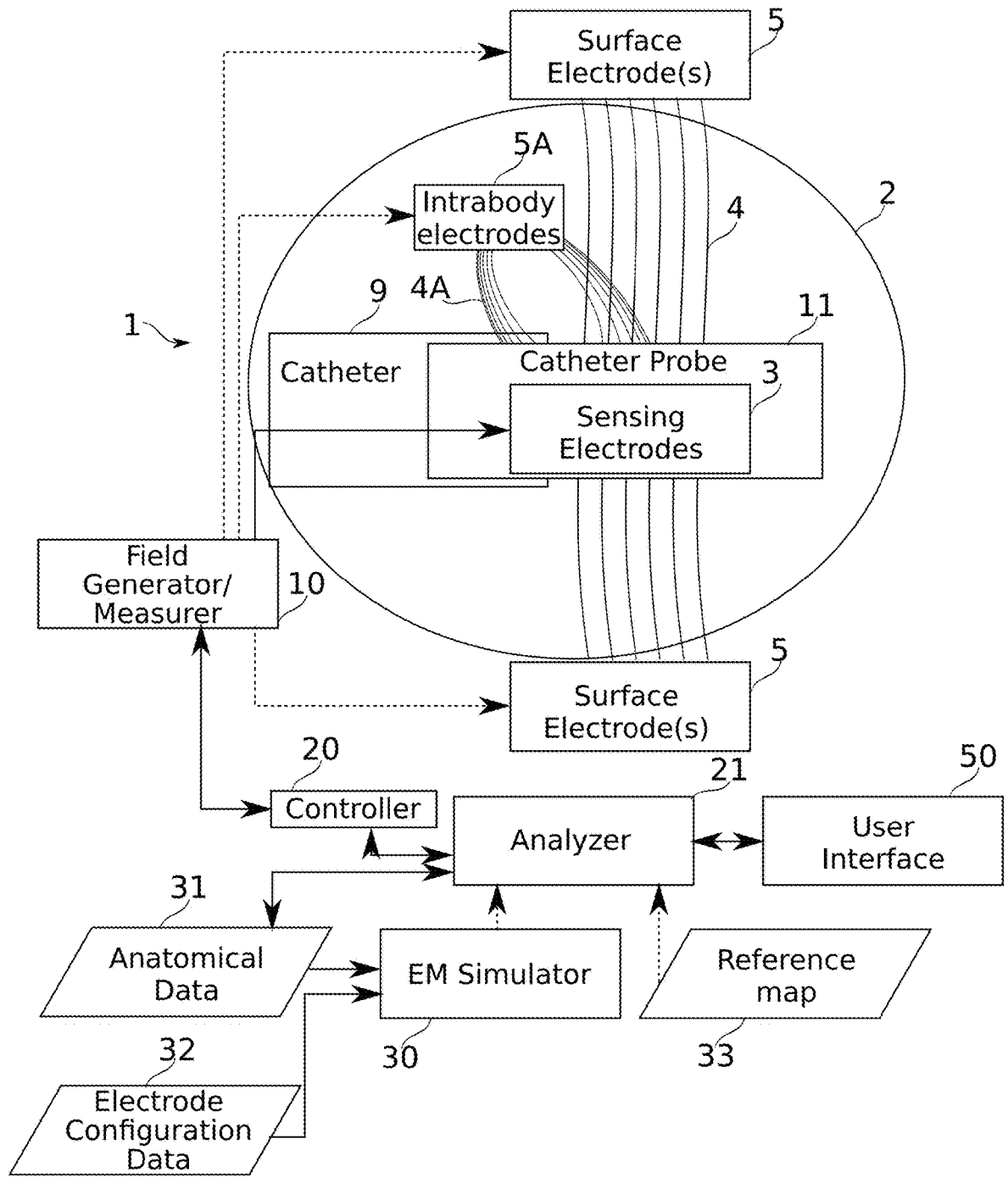
FIG. 4 schematically represents a system for obtaining electrical field measurements potentially indicating the position of an intrabody catheter, and assigning them to particular intrabody positions by determining and applying a transform using a pre-existing map associating intrabody electrical field measurements with intrabody positions, according to some embodiments of the present disclosure.

In some embodiments, the reference track voltages S are extracted (for example, extracted along characteristic tracks) from simulated intrabody electrical field potentials; prepared, for example, as described in relation to EM simulator 30 (FIG. 4). Optionally, the anatomical course of the simulated tracks is defined as an input to EM simulator 30 (e.g., defined on input 3D CT data). This provides a potential advantage for focusing computational effort of the simulation—for example, allowing extra simulation resolution to be provided along the tracks. Optionally, reference track voltages S are extracted from another source; for example, from previous procedures (of the same patient and/or one or more other patients), from earlier in the same procedure, and/or from atlas data.

In some embodiments, the reference intrabody voltages comprising the sequences of track voltages 111 are (at least initially) imperfectly registered to measured track voltages 110, so that pairing identification requires steps beyond identifying substantial equality. Optionally, the registration may need to be established de novo, e.g., due to potentially substantial variations in current measurement conditions from reference conditions.

There is, in some conditions and in some embodiments, enough general correspondence between a measured track and some available reference track that a pairing may be selected, e.g., from a limited number of initial possibilities such as may be defined by a set of pre-defined characteristic tracks. Additionally or alternatively, available track options for pairing are limited by knowledge that the catheter is traversing a path of at least approximately known length within the vasculature and/or heart. There are optionally further constraints on possible track pairing applied by automatic and/or manually supplied identification: for example, manual selection from a menu of options, prompting to get a user to move along a particular path, and/or automatic identification of characteristic landmark features (such as curvature around the aortic arch) which a given track $T_i$ includes.

In some embodiments, a sequence of reference track parameter values $S_i$ is paired to a sequence of measured track parameter values $V_i$ based on matching between voltage "features" along simulated and measured voltage tracks. For example, tracks where the direction of voltage change corresponds for each of three spatial axes of voltage measurement are optionally treated as "matching"; such matching may be considered in the pairing process. For example, a reference track may be paired with a measured track if they have one or more matching features.

In some embodiments, features having higher spatial frequency components (that is, changes in voltage and/or voltage slope which are relatively rapid as a function of catheter position, compared to slower changes, e.g., changes that oscillate few times or not at all along the track) are isolated for particular use in matching. The isolation may be, for example, by filtering (e.g., frequency thresholding). These features are potentially more likely to arise from local structure (providing a good target for registration), while also being potentially less sensitive to cumulative and/or certain systematic differences (like offset) in measured vs. reference track values.

In some embodiments, matching comprises accounting for potentially inhomogeneous sampling of voltage as a function of catheter translation along the track. For example, a catheter pullback rate may be subject to variability, particularly at the beginning and/or finish of a pullback. Pullback rate in the middle of a track potentially is less variable than at the ends. Optionally, in identifying a match between measured and reference tracks, greater weight is assigned to regions in the middle of the pullback, and/or to regions in the reference where the rate of change in voltage is constant (and which, optionally, may be associated with a more constant pullback velocity). Optionally, matches toward the track ends are fit by adjusting parameters of a pullback acceleration/deceleration model, for example, a polynomial or spine fit. Pullback rate may average, e.g., up to about 1 cm/s, 5 cm/s, 10 cm/s, 20 cm/s, or another larger, smaller, or intermediate average pullback rate.

Optionally, measurement-by-measurement registration is not required in order to form a match. A measurement track may vary slightly from a reference track (e.g, within the limits of the diameter of a blood vessel along the track, and/or within normal anatomical variation of the position of a blood vessel along the track), and this may lead to noticeable inconsistencies even after registration. Regions of sufficiently poor matching are optionally ignored in creating a mapping transform, and/or interpolated with a "best guess" based on regions that match well.

At block 114, in some embodiments, measured voltages V are mapped to positions on within a data representation of an anatomical space R by combining a mapping between measured and reference voltages $M_{V-S}$ with a mapping between reference voltages and positions in the anatomical space, wherein the mapping is designated $M_{S-R}$. In some embodiments, the data representation of the anatomical space R comprises an image (for example, a CT or MRI image). In some embodiments, the anatomical space R is generated from another source, for example, a reconstruction of a body lumen geometry based on electrical field measurements during a previous procedure or part of the current procedure.

Briefly, correspondences of measured voltages to reference voltages established along tracks (in $M_{V-S}$) are used to map the positions where the track voltages were measured into the space represented by R. This comprises making a further transformation using the reference voltage/position correspondences stored in $M_{S-R}$. $M_{S-R}$ may be saved in data structure block 113.

In some embodiments, mapping $M_{S-R}$ is produced by EM simulator 30. In simulation-using embodiments wherein R is image based, images used for mapping the simulated voltages may be the same image used in simulations, for example, CT image data, MRI data, or image data obtained using another 3-D medical imaging technique. Optionally, the data of reference voltage-to-position map 113 and the reference track voltages data 111 are both derived from the same data set of reference EM field measurements 406 (FIG. 5) produced by EM simulator 30.

Insofar as both reference map 113 and reference track voltages 111 may be derived from the same data representation (simulation, previous procedure-derived, or otherwise), their spatial relationships are known, so that the composition to obtain $M_{V-R}$ for regions at least near the measured tracks T—and potentially beyond, depending on the global applicability of the registration transform—is relatively straightforward. In some embodiments, the composition is performed via a calculated transform, selected so that parameters defined for the transform that maps T to R via S can also be applied to measured voltages in regions away from T. For example, the calculated transform may be a linear transform comprising parameters for scaling, rotation, and/or translation which can be applied uniformly to the transformed space. Alternatively, the calculated transform may be a non-linear (e.g., non-affine) transform. Other options for calculated transforms are discussed, for example, in relation to calculated transforms 408 of FIGS. 5-6.

In some embodiments, data describing conversion of measured track voltages to positions is stored (for example as a new mapping and/or as a transform) in data structure $M_{V-R}$ of block 115.

At block 116, in some embodiments, the $M_{V-R}$ data structure of block 115 is used as a basis for navigation. As a result of the pairing and transformation steps, the actual places (such as particular blood vessel and/or heart chamber positions) where measured voltages are taken are potentially in sufficiently close correspondence to the places in the data representation of an anatomical space to which corresponding reference voltages are associated, that voltage-defined position of a catheter probe 11 in the image can be used as an effective proxy for actual position of the catheter probe 11. Alternatively, the transform may be implemented to transform to a target different from the original reference space. For example, there may be a partial transform (post-processing) from the original reference space to some other anatomical space (e.g., one derived from recent imaging of the patient), in which case the data structure $M_{V-R}$ of block 115 is optionally expressed in terms of transformation into the other anatomical space. Optionally, the space R is "cloned" (optionally with post-processing) from the original reference space, and allowed to change dynamically as new measurements are obtained which potentially allow improvement on the initial fidelity of the registration (for example, as a method of updating used in relation to blocks 118, 121).

Registration, in some embodiments, extends beyond regions which have been directly aligned along tracks. In some embodiments, registration results can be treated as providing a global transformation for a body part of interest (such as an affine transformation), wherein the parameters of the transformation can be learned from registrations to simulated data applied along the extents of one or more (three, for example) pullback tracks. This allows further regions to be substantially registered to their true position (e.g., simultaneous virtual and actual contact with a cardiac or vascular wall) already upon being first visited. This optionally corresponds to registration by transform of more distal positions (relative to the positioning of the catheter), wherein the transform is created based on matching and registration of measurements made at more proximal catheter positions. For example, pullbacks within the right side of the heart and associated vasculature potentially establish an affine transformation that also brings the electrical field simulation of the left atrium of the heart into registration with actual measurements, as illustrated in FIGS. 3A-3B. In some embodiments, the effective range of the transform is more restricted; for example, generated from tracks within the left atrium (e.g., as in FIGS. 2C-2D), and optionally remaining restricted to a space within the left atrium substantially delineated by the extremes of those tracks.

As new voltage data continues to be measured (optionally along a track or not): at block 118, in some embodiments, the flowchart optionally branches to block 121 which updates map $M_{V-R}$ at data structure block 115 according to the new information received. For example, the update may be by finding a transformation that best registers all the readings measured to points in the image. The measured points may include the voltage readings used for the initial registration (which is now being updated), voltage readings measured from newly visited tracks, and/or voltage readings measured from points of any other track; or optionally (once a basic registration is established) positions away from a track. In some embodiments, readings measured during motion along a track are registered to points along that track. As may be understood from the above, new tracks may be obtained (indicated by optionally branching from block 118 back to before block 108).

At block 122, in some embodiments, a determination is made as to whether the navigation procedure is completed or not. If not, the flowchart returns to block 116. Otherwise, in some embodiments, the flowchart ends.

Reference is now made to FIG. 1B, which is a schematic flowchart of a method of assigning measured intrabody electrical field parameter values to positions within a cardiovascular anatomy, according to some exemplary embodiments of the present disclosure. FIG. 1B is a simplified version of FIG. 1A, for emphasis of major operations performed. Reference is also made to FIG. 1C, which is a schematic representation of aspects of block 130 of FIG. 1B, according to some embodiments of the present disclosure.

At block 130, in some embodiments, a plurality of reference sequences of electrical field parameter values (e.g., voltages) corresponding to values along tracks within one or more reference intrabody electrical fields are defined. In some embodiments, reference tracks correspond, for example, to the reference voltage tracks S of data structure block 111 of FIG. 1A.

With reference to FIG. 1C, some alternatives for sources 150 of reference tracks (optionally including the larger anatomical spaces they derive from) are now described, including mention of types and uses of 170 of reference tracks.

In some embodiments, a same-patient reference source 151 is used. Optionally, the same-patient source comprises data from a previous procedure 151A, and/or data from an earlier stage of the current procedure 151B.

In some embodiments, previous procedure data 151A is available because the current procedure is a follow up to an earlier procedure. For example, the current procedure may be to attempt a re-ablation several weeks after a previous ablation procedure having a non-satisfactory outcome. In this case, the tracks used to obtain at least initial registration are optionally "approach" type tracks 171; that is, tracks which have long baselines (such as those of FIGS. 2A-2B) and which may even be traversed priory to entry into the treatment area (e.g., the left atrium) itself. It may be expected, in this situation, that new measurements fit very well to previous procedure data upon registration based on approach-type tracks; insofar as, e.g., the anatomy is substantially identical, and/or electrode placements can be duplicated. A potential advantage of using the old data in the new procedure is improved localization of previous ablation targets, particularly if analysis has revealed positions at which problems with a previous ablation pattern are most likely to be the cause of an unsatisfactory treatment result. Knowing the previous ablation pattern in advance can also save time, e.g., by allowing a physician to reduce a need to measure conductivity and/or duplicate ablations. It is noted that the reference values associated with position data may also be associated, directly or indirectly with any other position-specific data available. For example, measurements of tissue state (electrical transmission properties, tissue vitality, scarring, ablation success, and/or edema time course, for example) made during a first ablation procedure are optionally available in a second procedure after registration using a transform created by measurement track/ reference track registration. Other position-specific data recorded may include positions at which a treatment modality (such as an injection or ablation electrode) was activated.

Optionally, in some embodiments, data from an earlier stage of the current procedure 151B is used as a reference source. The need for re-registration may occur, for example, because of movement of an intrabody catheter (e.g., out of the coronary sinus), contact changes (such as detachment) of body surface electrodes, drift in any other part of the electrical apparatus and/or patient state, or any other mishap that requires re-mapping. In this type of case, tracks selected may be "recovery" tracks 172, wherein the catheter is already positioned in the body part region of greatest interest for mapping, and the concern is to recover lost usefulness of already-obtained mapping data with a minimum of further disruption and loss of time. Recovery tracks 172 are optionally anchored on one end at the entrance position of the catheter to the region of interest (e.g., a septal fossa), and on the other end to readily visited and/or identified landmarks within the region of interest. FIG. 2C shows several tracks 281-285 which may be suitable as recovery tracks for a map of the left atrium that has been entered via the interatrial septum. Recovery tracks 172 may also be used in the case that registration of previous procedure data 151A is found to be insufficiently precise based just on the use of approach tracks 171, or recovery tracks 172 may be used for registration in the first instance.

Other sources of reference data include data from one or more different patients 153. Data from a matched procedure 153A (e.g., matched based on patient size, age and/or gender; optionally also matched based on anatomical variant type and/or similarities in pathology) may be registered using one or both of approach tracks 171 and recovery tracks 172. Additionally or alternatively, the data used is provided from an atlas which has been specifically prepared (optionally prepared from a plurality of patient sources, e.g., composited) as a source of reference data. In either case, differences in anatomical detail between the current patient and the reference source may make it more preferable to use recovery-type tracks 172, in order to get better sampling indicating features of non-linearities local to the region of greatest interest.

Finally, reference data may be obtained by simulation 155. Simulation may be based on anatomy of the same patient as is undergoing a current procedure; or a matched patient, for example matched from an atlas. At least two types of simulation may be distinguished, though each can be performed using the same simulation approaches (described, for example, in relation to FIG. 5, herein). One simulation type simulates electrical fields induced intrabody by body surface electrodes 155A. Another simulation type simulates electrical fields induced intrabody by intrabody electrodes 155B. In procedures using body surface electrodes, a common aim is to generate electrical fields which are substantially linear throughout a large range of positions. In this case, it may be preferable to perform registration based on approach tracks 171, so that registration is substantially complete even upon initial entry into the target region of greatest interest. In the case of intrabody electrodes, induced electrical fields may be configured to be most suitable for mapping uses only with the target region itself. There is potentially greater susceptibility to simulation and/or measurement error in regions further from the target region. Accordingly, it may be preferable to use "recovery" type tracks 172, which cross through the region of main mapping interest itself.

Returning to FIG. 1B: at block 132, in some embodiments, at least one sequence of intrabody electrical field measurements is measured from a catheter sensor (e.g., an electrode) as the catheter sensor moves along a track through a configuration of electrical fields corresponding to the reference intrabody electrical fields of block 130. In some embodiments, measured tracks correspond, for example, to the measured voltage tracks V of data structure block 110, produced from the operations of block 108 of FIG. 1A.

At block 134, in some embodiments, the measured sequence of intrabody electrical field measurements is registered to one of the plurality of sequences of reference electrical field parameter values. In some embodiments, the registration corresponds, for example, to the operations of block 112 of FIG. 1A.

At block 136, in some embodiments, the electrical field parameter values of further measurements of intrabody electrical fields away from the initial tracks are assigned to intrabody positions (for example, by application of a transform), based on the registering of block 134. In some embodiments, the adjustment corresponds, for example, to the operations of block 116 of FIG. 1A.

Examples of Characteristic Tracks

Figure 2A:
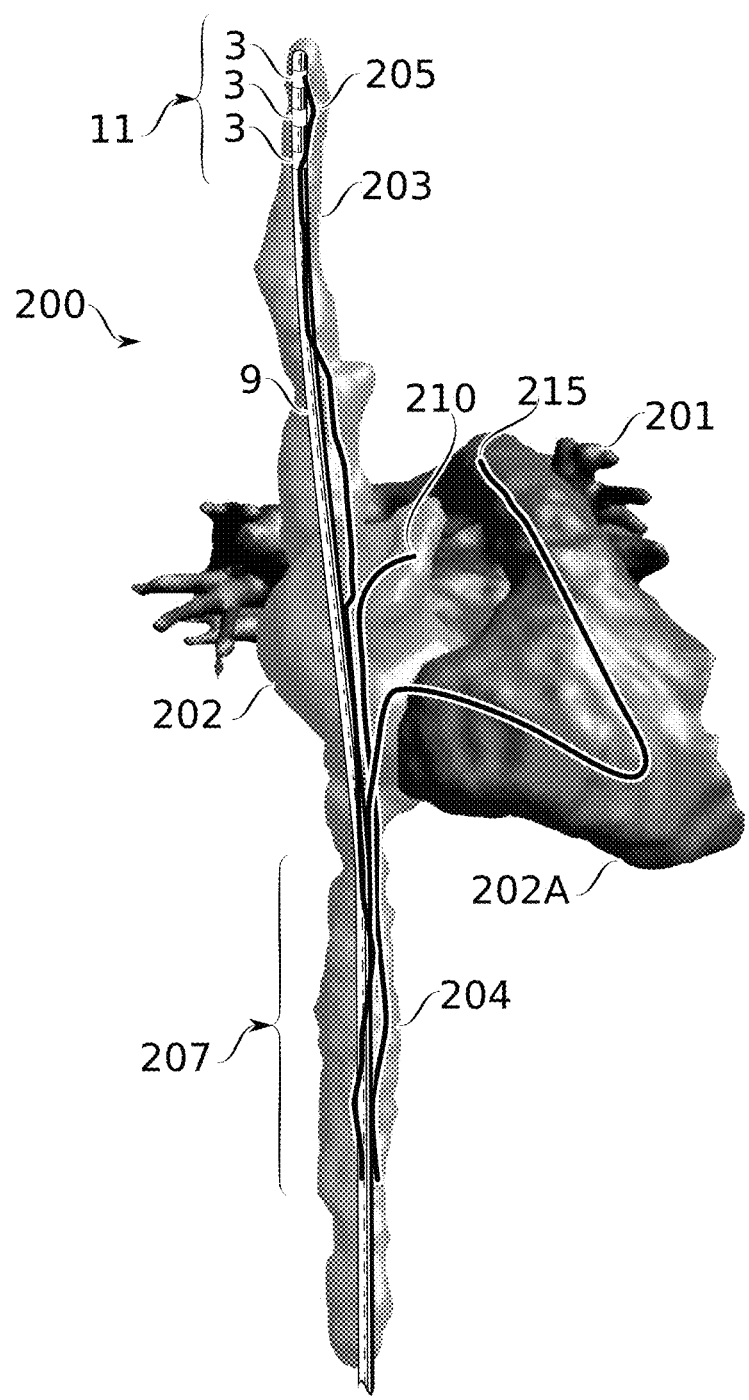
FIG. 2A schematically represents the courses of pre-determined catheter tracks through regions of the left atrium, right atrium, superior vena cava, and inferior vena cava of a heart, according to some embodiments of the present disclosure.

Reference is now made to FIG. 2A, which schematically represents the courses of pre-determined catheter tracks 205, 210, 215 through regions of the right ventricle 202A, right atrium 202, superior vena cava 203, and inferior vena cava 204 of a heart 200, according to some embodiments of the present disclosure. Also indicated is the left atrium 201.

Catheter tracks 205, 210, 215 comprise examples of how a catheter probe 11 may be moved through atrial chambers of a heart in order to quickly measure positioning information that may be used to help define tracking of subsequent catheter movements. Roughly, the tracks also correspond to catheter configuration before pullback (an example of a catheter 9 with probe 11 comprising three electrodes 3 is shown in a position poised for pullback along track 205), since pullback is in the direction back along the length of the catheter. The correspondence is not perfect, due, for example, to oscillations of the free catheter end, effects of catheter mechanical properties, etc.

Track 205, in some embodiments, comprises a pullback from a catheter position where a catheter 9 extends from the inferior vena cava (IVC) 204 to the superior vena cava (SVC) 203 via the right atrium (RA) 202. Thus, track 205 is through the sequence SVC-RA-IVC. Optionally, track 205 represents an initial pullback track, for example, one used with a catheter which reaches the heart via the inferior vena cava. This track provides the potential advantage of a wide base of sampling points with relatively little need for maneuvering, potentially increasing a likelihood of finding an unambiguous match between one or more features of actual electrical field measurements and corresponding features of simulated electrical field measurements. Even though track 205 is straight, the electrical fields that pass through it are potentially themselves characteristically distorted at one or more points, as discussed also in relation to FIGS. 3A-3B. In some embodiments, track 205 is used not only for fixing positions along the track to simulated electrical parameter data, but also for establishing an anchor region 207 held in common with other tracks, for example, tracks 210, 215.

Track 210, in some embodiments, begins from a position with the catheter tip curved slightly and advanced so that it lodges in the right atrial appendage (RAA). Accordingly, track 210 extends through the sequence RAA-RA-IVC. Pullback from a more medial position potentially helps to define a second axis for registration, as well as helping to define the height and/or medial extent of the right atrium.

Track 215, in some embodiments, begins from a position with the catheter passing from the right atrium to enter the right ventricle (RV) 202A, bending through it, and finally reaching to enter the main pulmonary artery (MPA). Pullback from this position (e.g., through the sequence MPA-RV-RA-IVC) potentially helps define a third axis (dorsal/ventral) for use in registration, as well as potentially defining dimensional extents of the right atrium that help to establish its general volume. The bend in the right ventricle in particular provides a potentially useful landmark due to likely inversion in the direction of voltage gradient changes in at least one axis as the catheter sensors reach and then turn to leave this region.

Figure 2B:
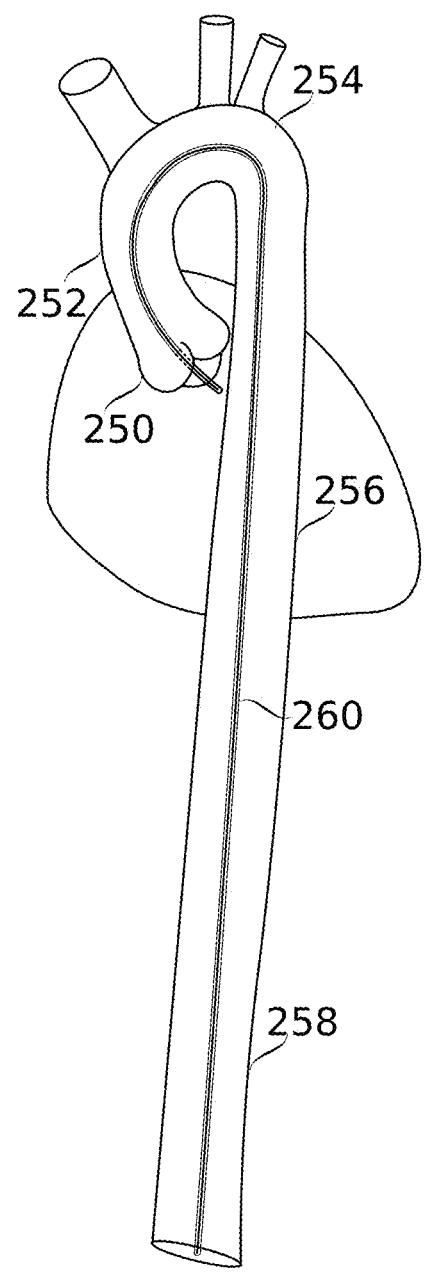
FIG. 2B schematically represents the course of a pre-determined catheter track through regions of the aorta, according to some embodiments of the present disclosure.
Figure 2C:
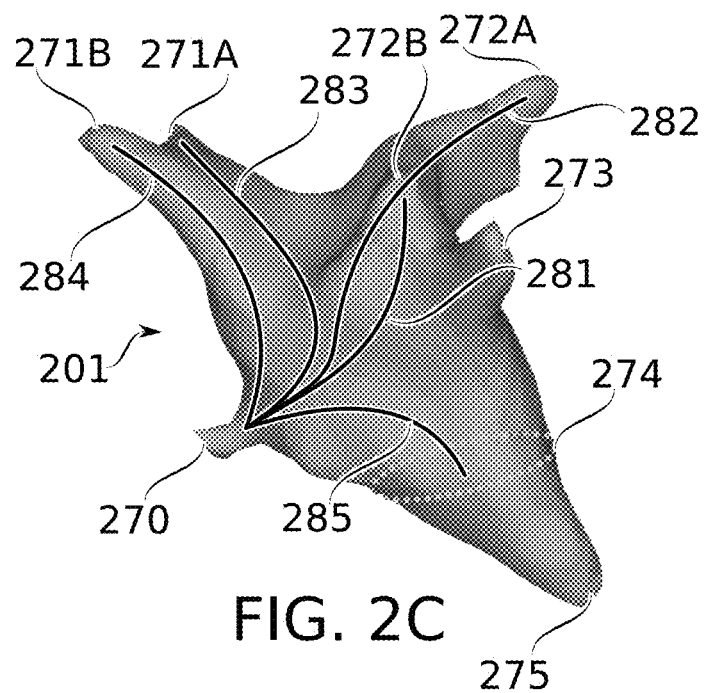
FIGS. 2C-2D schematically represent pre-determined catheter tracks to regions of the left atrium, according to some embodiments of the present disclosure.

Reference is now made to FIG. 2B, which schematically represents the course of a pre-determined catheter track through regions of the aorta, according to some embodiments of the present disclosure.

Catheter track 260 is an example of how a catheter probe 11 may be moved through portions of an aorta in order to quickly measure positioning information that may be used to help define tracking of subsequent catheter movements. Roughly, track 260 also corresponds to a catheter configuration (not shown separately) before pullback. The correspondence is not perfect, due, for example, to oscillations of the free catheter end, effects of catheter mechanical properties, etc.

Track 260, in some embodiments, comprises a pullback from a catheter position where a catheter 9 extends from the aortic valve 250 back through the ascending aorta 252, the transverse aortic arch 254, thoracic aorta 256, and abdominal aorta 258. This track provides the potential advantage of a well-defined landmark in the form of the crook corresponding to the transverse aortic arch 254. Optionally track 260 is defined at least partially as a "characteristic track", wherein the characteristic crook of the aortic arch is used as a landmark.

Figure 2D:
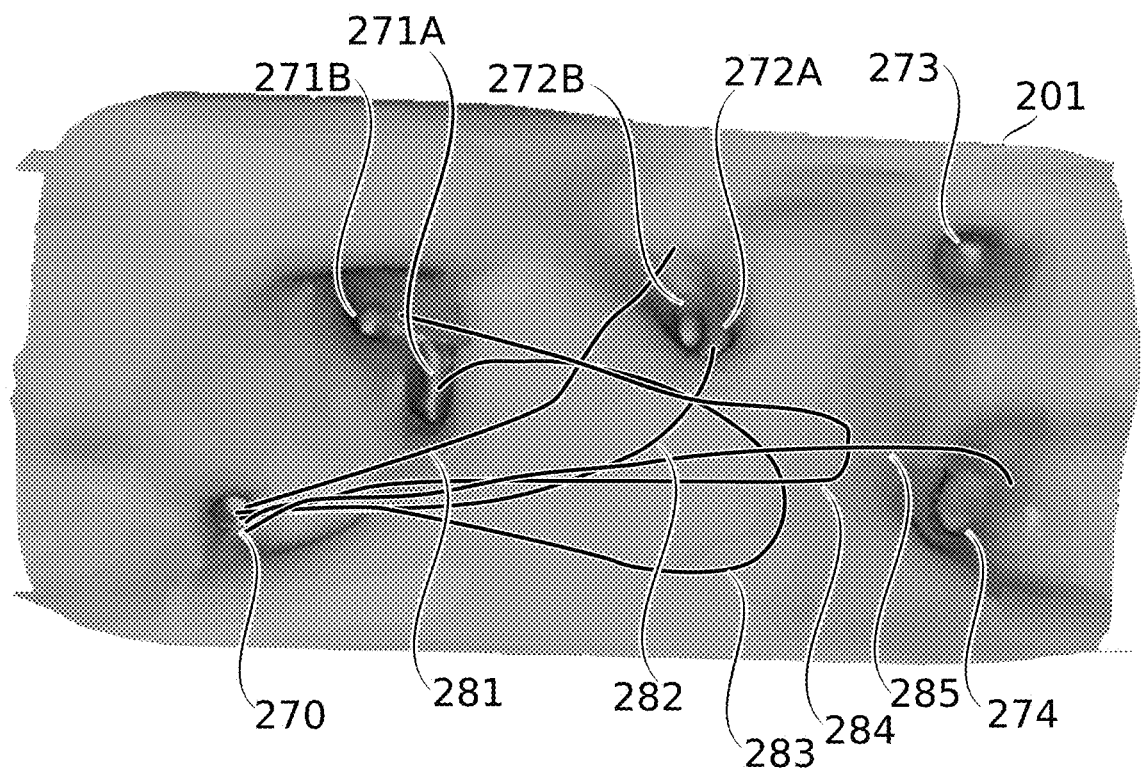
Figure 3A:
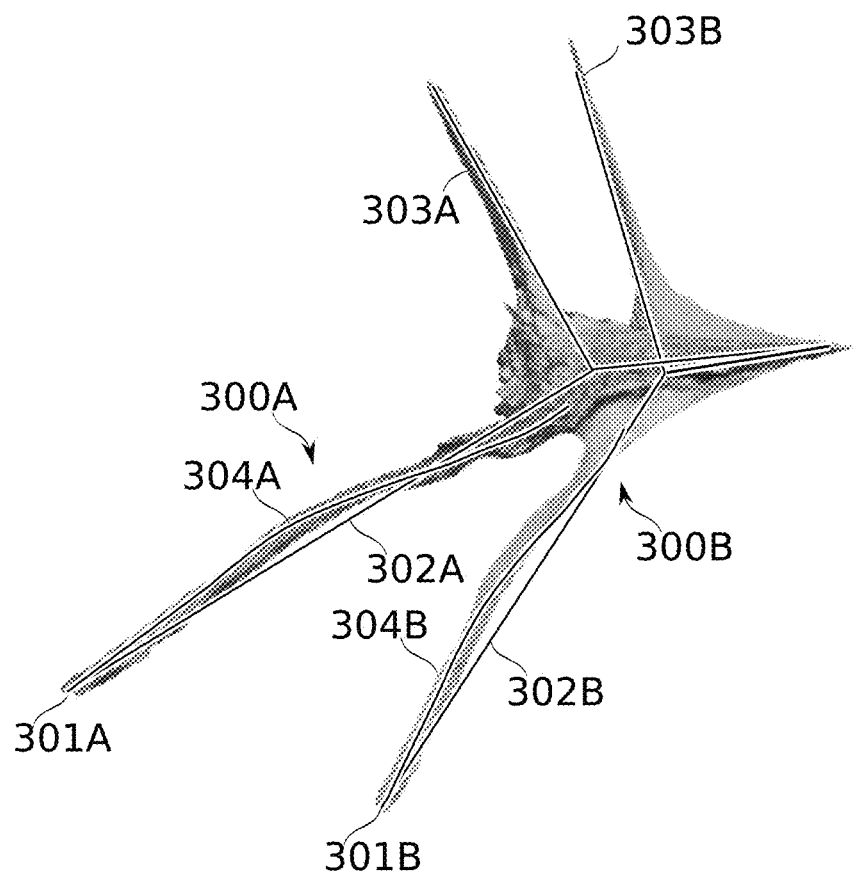
FIGS. 3A-3B schematically represent transformation of a first data representation of an anatomical space to a second representation of an anatomical space, based on transform parameters which register electrical parameter values along a reference track to corresponding measured electrical parameter values measured (e.g., in an active catheter procedure) along a track within an actual anatomy, according to some embodiments of the present disclosure.
Figure 3B:
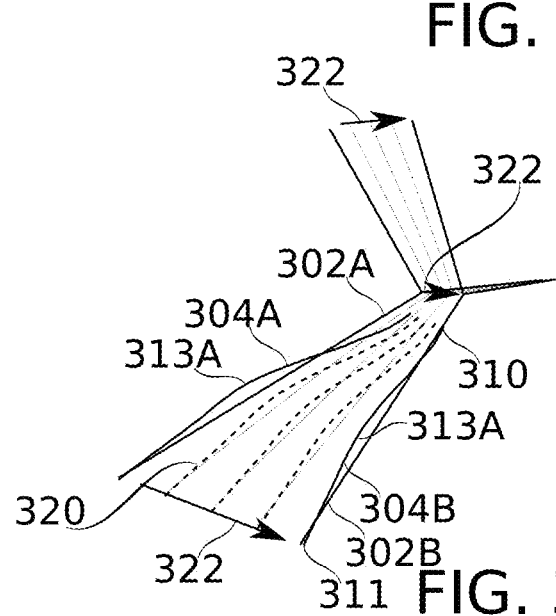

Reference is now made to FIGS. 2C-2D, which schematically represent pre-determined catheter tracks to regions of the left atrium 201, according to some embodiments of the present disclosure. FIG. 2C represents in three dimensions the semi-transparent interior lumenal surface of a left atrium 201. FIG. 2D represents the same interior lumenal surface "unwrapped" and viewed from its interior side, for example as described in U.S. Provisional Patent Application 62/445,368, filed Jan. 12, 2017, the contents of which are incorporated herein in their entirety.

In some embodiments, a catheter optionally enters a left atrium from a trans-septal crossing point 270 (e.g., the fossa ovalis). This provides one end of each of several tracks which connect trans-septal crossing point 270 to different landmarks of the left atrium. In particular:

Track 281 leads to the left superior pulmonary vein 272B.
Track 282 leads to the left inferior pulmonary vein 272A.
Track 283 leads to the right inferior pulmonary vein 271A.
Track 284 leads to the right superior pulmonary vein 271B. Tracks 283 and 284 appears to double back on themselves in FIG. 2D due to an artifact of the unwrapping.
Track 285 leads to the mitral valve 274.

Also indicated in the figures are positions of the mitral valve aperture 275, and the left atrial appendage 273. These features may also be used additionally and/or alternatively as landmarks for pre-determined tracks.

Taken together and/or in suitable sub-sets, tracks 281-285 extend substantially through and across the main dimensions of the left atrium. Accordingly, a transform which successfully registers these tracks is likely to also successfully register left atrium regions nearby and/or in between these tracks that comprise most or the entire left atrium interior which is of interest during a procedure for navigation, mapping, and/or treatment. The extent of useful registration "fill in" depends on the source relationship of the reference values and the measurement values. For example, if the two value types are from the same body part (of the same individual), registration may be useful (e.g., accurate to within 5 mm, 3 mm, 2 mm, 1 mm, or a larger, smaller, or intermediate value) throughout a region of interest for navigation and/or reconstruction. If from different individuals, initial track-guided registration may only be useful (as measured by accuracy, for example) within a limited distance from the original tracks, for example out to about 1 cm, 2 cm, 3 cm, or another larger smaller or intermediate distance.

In some embodiments, tracks may lead to, from, and/or among structures of a non-cardiac organ, for example a brain and/or ventricle thereof, kidney, and/or organ of the digestive tract.

Registration of Regions Beyond a Characteristic Track

Reference is now made to FIGS. 3A-3B, which schematically represent transformation of a first data representation of an anatomical space (atrial/vascular configuration 300A) to a second data representation of an anatomical space (atrial/vascular configuration 300B), based on transform parameters which register electrical parameter values along a reference track to corresponding measured electrical parameter values measured (e.g., in an active catheter procedure) along a track within an actual anatomy, according to some embodiments of the present disclosure.

As shown in FIGS. 3A-3B, atrial/vascular configurations 300A, 300B are modeled on porcine right atrium and connecting regions of the superior and inferior vena cava (segments 302B, 302A extend through the inferior vena cava; segments 303B, 303A extend through the superior vena cava). For purposes of this description, configuration 300B represents the lumenal shape (defined by surrounding cardiovascular tissue) of an actual space through which a catheter probe 11 navigates on the basis of electrical field property measurements (voltage measurements will again be used as an example in the descriptions that follow).

Configuration 300A represents the lumenal shape of a reference region (simulated, or from a previous procedure, for example) which is available for use in guiding voltage-guided navigation through actual configuration 300B. Distortion of configuration 300A relative to configuration 300B is due to initial non-alignment between reference voltages and voltages which are actually present to be measured. The non-alignment may be due, for example, to actual body surface and/or intrabody electrode impedances (or another property such as position) being different between reference and actual conditions, and/or to use of anatomical information in generating the reference space which only approximates, rather than exactly reflects, the anatomy of the procedure (e.g., anatomical information from an anatomical model bank). If the reference data is derived from simulation, there may also be errors in how 3-D image data was initially processed, and/or errors in the assignment of dielectric properties of tissue.

Thus, for example, the positions of voltages assigned by the pre-registration reference data to the inferior vena cava lie laterally displaced from where they should be. In some embodiments of the invention, the two configurations 300A, 300B are brought into alignment by application of a suitable calculated transform, which may be expressed in any suitable mathematical and/or computational form, e.g., as a linear transform, a non-linear transform such as a polynomial transform, a data array, a lookup table, etc.

In some embodiments of the invention, calculation of the transform is based on finding a best match (under some kind of registration rules) between actual voltage measurements made along one or more catheter motion tracks (for example, track 304B), and a corresponding track in the model, for example, simulated track 304A. For purposes of discussion, just one simulated/actual track pair 304A, 304B is considered, but it should be understood that there are optionally a plurality of either tracks to consider; and the transform may improve as more tracks are taken into account.

A "best match" is optionally defined as a match with the least error found under the implemented conditions of comparison between two tracks (reference vs. measured tracks, for example). The comparison may be a direct comparison, and/or a comparison after transformation; for example transformation to remove offsets, filter out spatial frequencies that do not contribute to matching, and/or transformation to adjust geometry according to constraints of a particular patient such as size and/or other anatomical variations. Error is optionally defined by any suitable metric, for example, least mean squared difference. Additionally or alternatively, best matches may be defined or further defined as matches which satisfy (and/or best-satisfy from among alternatives) other criteria for track matching and/or registration; for example as described herein, and in particular, in the following paragraphs relating to matching and registration.

In some embodiments, matching is performed by determining a best fit achieved by a particular transform type. It should be understood that the definition of a "best" or "optimal" fit or transform is relative to the implementation and assumptions of the algorithm implemented for optimization. The optimal transform found by an algorithm may be dependent, for example, on the selection of stopping conditions, potential for reaching a local minimum result, etc.

In some embodiments, a best fit uniform linear transform is determined, and the residual error used to judge which candidate track is the most likely candidate. Optionally, the best fit transform is also used as a transform to register the two tracks. Additionally or alternatively, final registration comprises use of a different transform or transform type, for example, one including terms to account for non-uniform stretching, errors in the correlation of catheter position and catheter voltage during pullback, etc. The transform may be affine or non-affine. In some embodiments, registration uses a coherent point drift (CPD) model to match measured and reference electric field parameter values. A potential advantage of using an identify-then-register approach is to avoid track selection errors due to over-fitting to the initial candidates, while keeping the ability to make finer matching adjustments once matching tracks have been identified.

Optionally, matching and/or registration comprise identifying constraints which define corresponding places on each track to map to one another. These places are optionally defined in different ways. For example, one or more of track endpoints 310, 311 may be well-defined by a structural limitation which geometrically limits movement of the catheter. The descriptions of tracks 205, 210, and 215 of FIG. 2A, and track 260 of FIG. 2B point out specific examples of track features which may be used to facilitate alignment of actual motion to a simulated track.

Optionally, identifying landmarks are sufficiently stereotypical that matching and/or registration to reference tracks can be dispensed with. For example, a measured sequence of voltage measurements optionally matches a stereotypical feature of voltage measurement tracks which localize it to a particular offset passing through the main pulmonary artery. Then voltage values of the measured track are optionally directly "inserted" to the appropriate anatomical location of an anatomically simulated electrical field, and the transformation of the simulated electrical field overall is carried out based on a transform that maps the measured voltage measurements to the simulated voltage measurements it extends along.

In some embodiments, a track endpoint is defined by a place where a non-geometrical parameter can be measured (e.g., onset of detectability of electrical excitations and/or excitability of the heart). In some embodiments, regions along the track are distinctive. For example, the curvature inflection point 313A of actual catheter track 304B corresponds to inflection point 313B of simulated track 304A.

Moreover, even a geometrically straight (or substantially straight) track is potentially "curved" in an electrical parameter space such as voltage. A catheter moving along a sufficiently long track, even a straight one, is liable to experience in one or more dimensions different rates of, for example, change in voltage as a function of distance. Potentially, changes in voltage are even non-monotonic. This is illustrated by recognizing that even in a uniform medium, electrical isopotential lines generated between two closely spaced electrodes (e.g., intra-body electrodes placed in the cardiac sinus for inducing navigating fields therefrom) tend to be curved. For example, a track running substantially tangential to a curving iso-voltage line at some point will measure regions of voltage change in opposite directions on either side of the tangent point. In a non-uniform medium, local tissue differences in dielectric properties (e.g., differences among tissue types such as bone, lung, muscle and/or blood) will tend to introduce an additional degree of curvature, potentially even "waviness", in the electrical field structure.

In some embodiments, inflection points defined by voltage change as a function of track position are used in the identification of matching tracks, and/or to align them. The inflection points are optionally determined, for example, as zero crossings in a first (velocity), second (acceleration), or higher-order derivative of measurements along an axis of one or more electrical fields being measured.

In some embodiments, a simulated electrical field potentially includes distortions due particularly to nearby dielectric inhomogeneities (e.g., nearby bones and/or voids in the lung). These features provide a potential target for feature matching between actual and simulated electrical field measurements. In some embodiments, electrical field measurement and/or simulation data are spatially filtered (e.g., filtered as a function of position along a track) to isolate certain spatial frequency components of the electrical field distribution. In particular, higher spatial frequency components (e.g., components corresponding to variations on the scale of about 5 millimeters to about 5 centimeters) are potentially the components most affected by local features of dielectric inhomogeneity (e.g., boundaries between lung and fluid, muscle and bone, etc.). Optionally, a best-fit transform is made to isolated features such as high-frequency components of the track voltage sequence, rather than to the entire voltage signal.

In some embodiments, mapping transformations are determined at least partially by use of known displacement along the measurement track during movement of the catheter; obtained, for example, by directly measuring how far the catheter travels. The measurement is performed, for example, by noting by how much the catheter is advanced or withdrawn at the time of each electrical field measurement while following the track. This may be optionally noted at the beginning and/or end of the tracking movement; and optionally at intermediate positions during the movement, for example, continuously. In some embodiments, pullback velocity is treated as substantially constant without a requirement for actual measurement. Alternatively, the transform used to fit measured measurement data to simulated measurement data includes terms that allow the velocity itself to be fitted, for example as a polynomial or spline.

Figure 5:
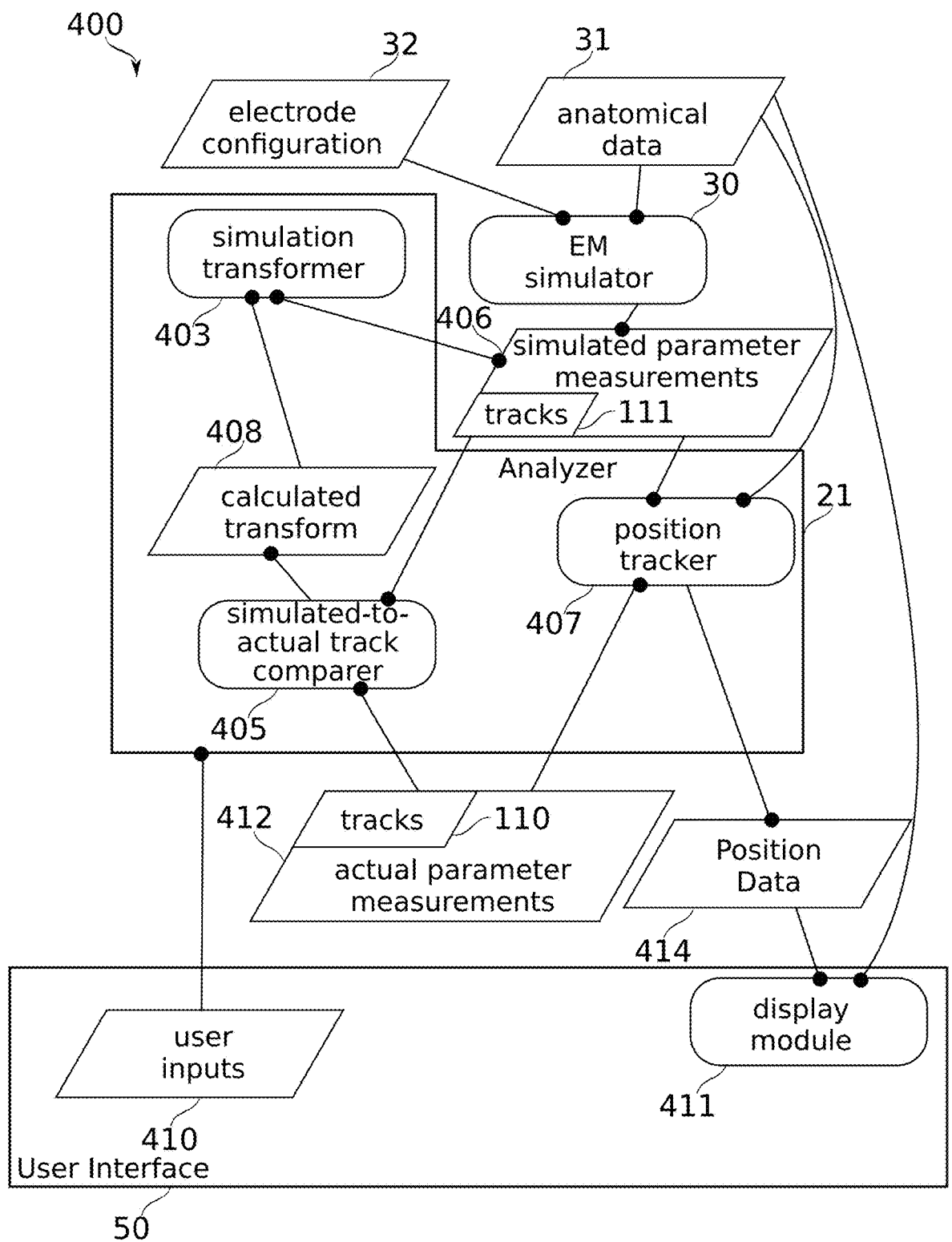
FIG. 5 schematically represents software-implemented modules and data structures of a system for measuring electrical field measurements potentially indicating the position of an intrabody catheter, and assigning them to particular intrabody positions, by determining and applying a transform using a pre-existing simulated map associating intrabody electrical field measurements with intrabody positions, according to some embodiments of the present disclosure.
Figure 6:
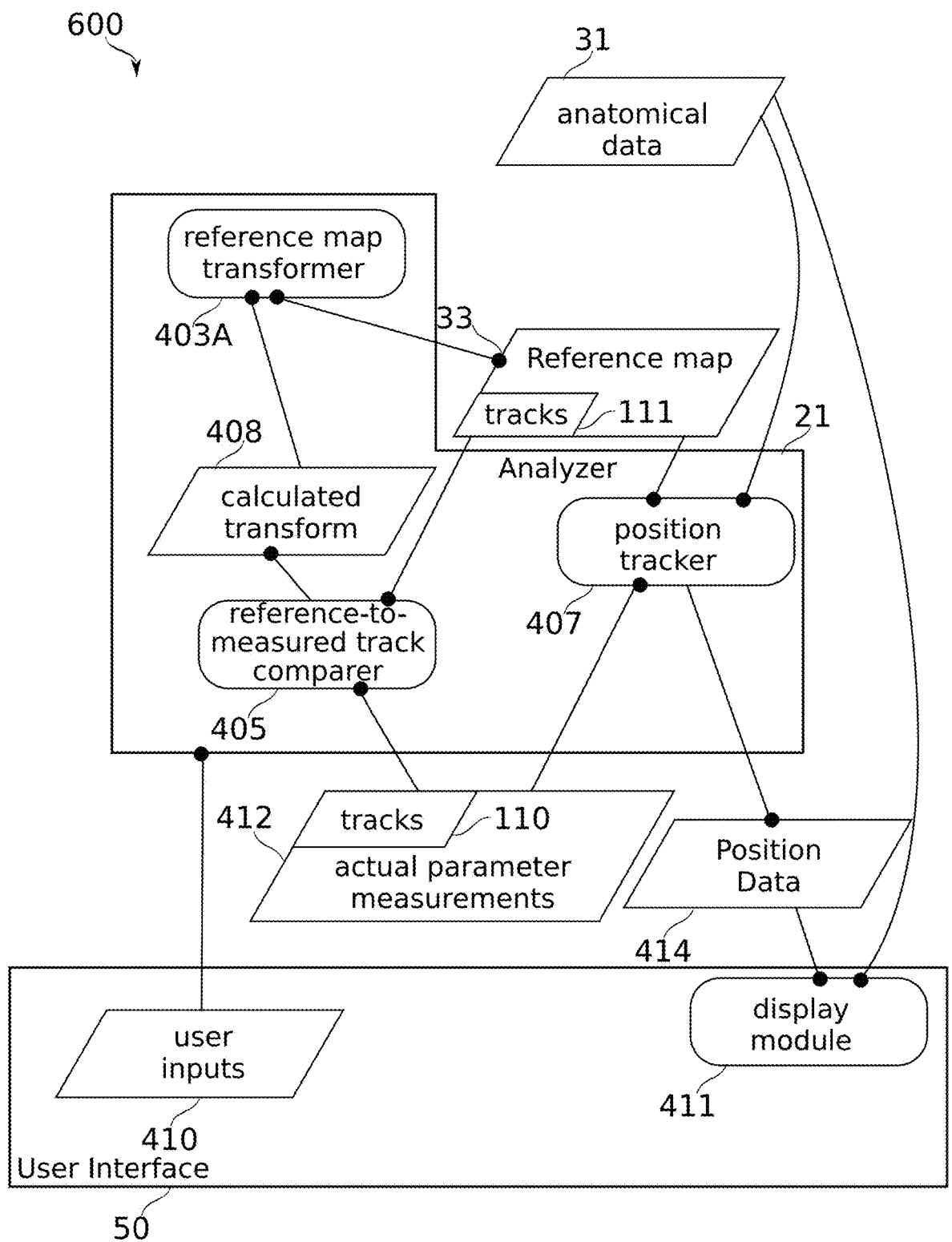
FIG. 6 schematically represents software-implemented modules and data structures of a system for measuring electrical field measurements potentially indicating the position of an intrabody catheter, and assigning them to particular intrabody positions by determining and applying a transform using a pre-existing map associating intrabody electrical field measurements with intrabody positions, according to some embodiments of the present disclosure.

Once homologous extents of at least one reference track and one measurement track from a current procedure have been paired, a transform may be calculated (for example to create a calculated transform 408, described for example in relation to FIGS. 5-6). Optionally, the transform is one calculated as part of the pairing. For example, if a best-fit (e.g., error-minimizing) approach is used to perform match identification, then the transform achieving the best fit (least error) is optionally used directly.

For purposes of illustration, dashed lines 320 of FIG. 3B represent the effect of applying the transform as "motion" between steps converting path 304A into 304B, but ordinarily the transform would be applied in an atomic (that is, concerted or single-step) operation. The calculated transform optionally comprises alteration of the spatial distribution of voltages and/or of the anatomy. This is useful, for example, when the differences between reference and measurement are characteristic of an affine transformation of the electrical field, or at least may be usefully so-approximated within the region of greatest interest for catheter navigation. Additionally or alternatively, the voltages themselves are transformed in place (e.g., offset, scaled and/or transformed non-linearly; optionally the transform applied at each position itself varies according to parameters defined as a function of spatial position). Optionally, the transform is non-rigid.

In some embodiments, the actual anatomy will be correctly represented in the reference data representation of the anatomical space; e.g., well-known from imaging data and/or previous reconstruction. In the case of a data representation of the anatomical space based on an anatomy from an atlas or library, however, there may be transformation particularly directed to anatomical registration applied (additionally or alternatively). Optionally, transformation of voltages can be either from active procedure measurements into reference measurements or the reverse. However, it may be preferable to convert the reference measurements (and their associated positions) to be more like the active procedure measurements; for example since this potentially preserves the direct meaning of other measurements like physical distance along the catheter.

The three-segment frameworks 302B and 302A comprise corresponding simplified stick-model representations of lumenal shapes 300B, 300A, and are used in FIG. 3B to illustrate a more global step of transformation, corresponding, for example, to operations within block 136 of FIG. 1B. Global transformation is shown for purposes of illustration. Optionally, transformation is actually applied in portions: for example, one measurement at a time (e.g., assigning positions to each new measurement as it is obtained). In some embodiments, even though there is no track data extending through all of the region of navigational interest, calculated transform 408 is formulated so that it can be applied (transformation application is indicated by arrows 322 and associated dotted lines) to registration throughout the simulated region. A simple example of this is a linear transform comprising uniform rotation, translation, and/or scaling (optionally with different parameters for each spatial axis) throughout the simulation space. Such a transform may be useful when the main differences within a particular pairing of traversed/reference anatomical spaces, and measured/reference electrical fields are from global parameters, e.g., the anatomy is the same, but there are changes in voltage gradient strength and offset. Once correct linear transform parameters are known for a part of two suitably corresponding spaces, regions in all parts of the space can be re-reregistered, including parts beyond sampled track regions.

In some embodiments, a transform is non-linear, e.g., non-rigid. Non-rigid transforms may be more adaptable to local differences in a navigated intrabody space from the reference body part shape and/or electrical field parameter value distribution, generally in exchange for more transform parameters that need to be selected, and potentially less accuracy in regions distant from the tracks used in registration (e.g., depending on the validity of extrapolation assumptions). However, effects of transform parameters which adapt non-rigidly to local variations in registration scale/offset/orientation are optionally implemented so that they are effectively superimposed on the effects of parameters describing a global (e.g., best-fit average) transform.

Non-rigid transforms such as coherent point drift-based transforms have a potential advantage for increasing the fidelity of the registration, particularly for body part regions close to a track and/or locatable by interpolation through spaces positioned between tracks. Examples illustrating a range of possible non-linear transforms are described in relation to calculated transforms 408 and FIGS. 5-6.

Systems for Registration of Electrical Field Simulations to Measurements

Reference is now made to FIG. 4, which schematically represents a system 1 for obtaining electrical field measurements potentially indicating the position of an intrabody catheter 9, and assigning them to particular intrabody positions by determining and applying a transform using a pre-existing map associating intrabody electrical field measurements with intrabody positions, according to some embodiments of the present disclosure.

In some embodiments, a catheter probe 11 comprising the catheter electrodes 3 is introduced intrabody to be navigated to one or more target regions (for example, to chambers of a heart for diagnostic assessment and/or delivery of treatment) by means of a catheter 9. In some embodiments, intrabody electrical fields 4 and/or 4A are sensed for electrical field-guided navigation of a catheter probe 11. In some embodiments, sensed parameters of intrabody electrical fields 4, 4A are used in determination of the intrabody position of catheter probe 11.

In some embodiments, system 1 comprises an electrical field generator and measurement device 10, connected to drive current to and/or sense electrical potentials experienced by one or more catheter electrodes 3. In some embodiments, electrical fields 4 are induced by a set of body surface electrodes 5 to induce at least one (e.g., three or more crossing) time-varying electrical field 4 therebetween. Additionally or alternatively, in some embodiments, a plurality of electrical fields 4A is induced by a set of intrabody electrodes 5A to induce intrabody time-varying electrical fields. The two different approaches (body surface electrode vs. intrabody electrode) have different potential advantages and disadvantages for guiding intrabody navigation.

The body surface electrode approach may be technically less demanding to set up in terms of initial electrode positioning (e.g., directly applied electrode patches 5 vs. electrodes 5A maneuvered intrabody on a dedicated catheter), and may optionally be set up in pairs that approximate axes of 3-D space, including relatively linear electrical field regions that can simplify the task of converting electrical field measurements into position estimates.

In some embodiments, body surface electrodes 5 are externally applied, for example, to the body of a patient. Upon activation of electrical field generator 10, fields 4 are induced in tissue 2 (for example, tissue of a patient's body in the region of the heart or other region of navigation).

Optionally, the number of catheter electrodes 3 is, for example 1, 2, 3, 4 or more electrodes. Where two or more electrodes are present, sensing from each optionally allows distinguishing of an orientation of the catheter probe 11 as well as a three-axis position in space. Optionally, the number of body surface electrodes is, for example, 2, 3, 4, 5, 6, 7, or 8 electrodes. In some embodiments, at least some body surface electrode pairs are arranged to generate one or more electrical fields defining a spatial axis for navigation of the catheter 9. Optionally or additionally, one or more electrodes (intrabody and/or body surface) are used in sensing of tissue properties for tissue assessment, for example dielectrically, and/or for the delivery of tissue ablation energy (e.g., for RF ablation of tissue).

Intrabody electrodes provide a potential relative advantage by allowing higher field gradients to be focused near an intrabody region of particular interest (given that electrical current is generally limited for safety reasons), potentially increasing position detection resolution. Intrabody electrodes are also potentially more predictable and/or stable in the electrical fields they induce, since, e.g. they are not affected by issues such as perspiration and/or de-adherence, and since they are less influenced by anatomical structures distant from the intrabody region of interest. In some embodiments, intrabody electrodes 5A are internally positioned, for example, in the coronary sinus, and/or at another intrabody position. Upon activation of electrical field generator 10, fields 4A are induced in tissue 2 (for example, tissue of a patient's body in the region of the heart or other region of navigation).

Optionally, the characteristics of the time-varying electrical field are chosen to be appropriate to a measurement function which is to be performed. Typically (for measurement functions), the frequencies of the electrical field used are in the range of 40 kHz to 2 MHz. In some embodiments, use of multiple frequencies allows sampling of frequency-dependent impedance properties throughout a frequency range. Optionally, the number of frequencies used is, for example, 10 or fewer frequencies. Optionally, the number of frequencies used is, for example, 5 or fewer, 15 or fewer, 20 or fewer, or 30 or fewer. Optionally, the frequencies are distributed evenly throughout the full range of frequencies chosen. Optionally, frequencies chosen are concentrated in some particular range. For example, for lesion assessment, frequencies in the upper portion of this range are optionally used (for example, frequencies in the range of 1 MHz to 2 MHz). Frequencies of about 10-100 kHz are typically used in electrical field-based intra-body navigation applications.

Applied voltages between surface electrodes 5 and/or intrabody electrodes 5A are preferably in the safe range for use in humans, for example, 50-500 millivolts. In particular, a typical maximum safe current is about 1 milliamp, with a typical circuit resistance of about 100 a Resulting field strengths are in the range, for example, of several millivolts per centimeter; for example, 10 mV/cm, 20 mV/cm, 30 mV/cm, or another larger, smaller, or intermediate value. In some embodiments, the field gradient required to achieve reliable navigation is determined by the ability to distinguish between at least two electrodes (e.g., the two electrodes positioned furthest from one another) on a navigating catheter probe. In some embodiments, for example, distinct voltages measured between at least two such electrodes are used to determine of an orientation of the electrode-carrying probe. In some embodiments, a minimum voltage distinguishable between the two most mutually distant electrodes on an electrode-carrying probe (for some suitable assumption of signal-to-noise conditions) defines a lower bound for an acceptable field strength. The minimum voltage may be, for example, in a range between about 1 mV and 10 mV, depending on factors such as signal-to-noise ratio.

In some embodiments, configuration of body surface electrodes 5 (size and position, for example) and/or intrabody electrodes 5A is according to parameters which are selected as part of procedure planning.

Optionally, and based on either type of field-inducing electrode (body surface or intrabody) electromagnetic simulation (EM simulation) is used for predicting what electrical field properties (e.g., voltage potentials) will be sensed at intrabody positions through which catheter probe 11 is navigated. Optionally, the EM simulation is used during a catheterized procedure, for example in order to guide the catheter probe 11.

Analyzer 21 optionally uses as input one or both of outputs from EM simulator 30, and reference map 33.

In some embodiments, an EM simulator module 30 is provided as part of the system. Optionally, the EM simulator 30 is configured to perform simulation based on anatomical data obtained from the patient (3-D CT or MRI image data, for example). Optionally, the anatomical data is obtained for one or more other patients (e.g., as data from an anatomical atlas), and matched to a specific patient undergoing a procedure based on parameters including, for example, age, gender, weight, and/or overall body morphology. In some embodiments, the anatomical data are segmented into regions of different tissues having potentially different electrical field propagation properties (e.g., different dielectric properties such as permittivity and conductivity). The result of the simulation is a mapping which links simulated electrical field parameter value to Permittivity and conductivity values of many tissues, including heart, have been published. It should be noted that these properties are roughly linear in log:log plots over ranges of a few hundred kHz within the range mentioned, which potentially allows distinctions among tissue types to be made without a requirement for dense frequency sampling. In some embodiments, the simulation is also based on electrode configuration data 32, describing, for example, the size, shape, placement, and/or impedance characteristics of surface electrodes 5, and/or intrabody electrodes 5A. Exemplary commercially available simulation tools that may be used as a framework for generating simulations described herein include: Sim4Life (available from Zurich Med Tech), COMSOL Multiphysics®, and CST Design Studio™.

In some embodiments, reference electrical field parameter values and their distribution through a position in a data representation of anatomical space comprise a reference map 33, derived from a source other than EM simulator 30. For example, reference map 33 may comprise electrical parameter values measured in a previous procedure within the same and/or one or more different patients. Optionally, the electrical parameter values are measured previously within a current procedure that needs re-calibration, e.g., due to potential drift and/or incident that degrades an original frame of reference. The data representation of an anatomical space in reference map 33 comprises, for example, image data (e.g., CT, MRI, and/or reconstructed 2-D angiography data). Additionally or alternatively, the data representation of an anatomical space comprises a spatial reconstruction from another data source, for example, reconstruction based on electrical field sensing by a moving intrabody electrode.

In some embodiments, user interface 50 is provided with controls allowing selection of how controller 20 uses the other inputs to the analysis—for example, to review and/or correct alignment, adjust model parameters, and the like. The interface is also optionally used for controlling and/or displaying information from EM simulator 30.

In some embodiments, the electrical field generation and measurement device 1 is under the control of controller 20, which itself is optionally under user control through user interface 50. Controller 20 optionally comprises a computer with a processor (CPU or other digital hardware) operating according to programmed code. Controller 20 is described herein as a multi-functional module; however, it is to be understood that functions of controller 20 are optionally distributed among two or more modules of the system.

In some embodiments, electrical field generation by field generator/measurer 10, for example, to establish navigation fields, is under the control of controller 20. Optionally, measurements from field generator/measurer 10, for example, those used in measuring position-dependent electrical field properties sensed by catheter electrodes 3, are communicated back to the controller 20.

In some embodiments, system 1 comprises a measurement analyzer 21. Analyzer 21 comprises a processor, memory (optionally, non-volatile memory) storing data, and memory (optionally, non-volatile memory) storing processor instructions which, when executed, operate the processor to perform functions described in relation to analyzer 21 herein. In some embodiments, measurement analyzer 21 relates received electrical measurements to one or both of reference map 33 and simulated electrical field data provided by EM simulator 30, to convert electrical measurements into position(s) of catheter electrode 3. Optionally the conversion is also based on information about the positions of body surface electrodes 5, and/or anatomical data 31 describing electrical field propagation properties of tissue 2 and/or target region 6.

In some embodiments of the invention, conversion by measurement analyzer 21 is achieved and/or refined by the mapping of voltages measured along tracks to voltages calculated along simulated tracks, for example as described in relation to FIGS. 1A-1B. Examples of software modules and data structures used by measurement analyzer 21 and related components are described in relation to FIGS. 5-6.

Optionally, the model is refined by additional data received by electrode sensing, for example, sensing from catheter electrodes 3 and/or body surface electrodes 5.

Reference is now made to FIG. 5, which schematically represents software-implemented modules and data structures 400 of a system 1 for measuring electrical field measurements potentially indicating the position of an intrabody catheter, and assigning them to particular intrabody positions, by determining and applying a transform using a pre-existing simulated map associating intrabody electrical field measurements with intrabody positions, according to some embodiments of the present disclosure. Reference is also made to FIG. 6, which schematically represents software-implemented modules and data structures 600 of a system 1 for measuring electrical field measurements potentially indicating the position of an intrabody catheter, and assigning them to particular intrabody positions by determining and applying a transform using a pre-existing map associating intrabody electrical field measurements with intrabody positions, according to some embodiments of the present disclosure. Since FIGS. 5 and 6 represent alternative implementations optionally sharing most features, they are described together, with features specific to a particular implementation noted.

Software-implemented modules (or at least partially software-implemented modules) also described in relation to FIG. 4 include measurement analyzer 21, EM simulator 30 (FIG. 5) and user interface 50. Reference map 33 (FIG. 6) is also shown in FIG. 4. Optionally, user inputs 410 are used to guide, modify, and/or signal acceptance of any of the operations of measurement analyzer 21; for example, to identify epochs of catheter probe movement which should be treated as yielding data for tracks 110, to confirm/adjust automatic detections and/or identifications of actual and simulated tracks 110, 111, or for other operations relating to the operation of the system such as selection of operational mode, calculated transform 408 type (linear or non-linear, for example), etc.

Data structures also described in relation to FIG. 4 include electrode configuration 32 (FIG. 5), and anatomical data 31. Edges link modules and data structures along main paths of data use and/or modification. Dark circles represent, in some embodiments, use of an edge-connected data structure as an input (if falling on round-cornered blocks representing software modules), or creation/alteration of the data structure (if falling on a rhomboid representing a data structure).

In some embodiments of the invention, an output of electrical simulator 30 (FIG. 5) comprises simulated electrical field measurements 406 (FIG. 5), which relate simulated spatial positions to corresponding simulated electrical field measurements (for example, expressing simulated voltages as a function of position in three spatial dimensions). Additionally or alternatively, an existing reference map 33 (FIG. 6) is used, relating positions in another data representation of an anatomical space to corresponding electrical field measurement values.

In some embodiments of the invention, position tracker 407 is a component of analyzer 21 configured to accept actual electrical field measurements 412 such as voltages (provided, for example, from controller 20). Position tracker 407 uses those actual electrical field measurements 412 to determine the spatial position of catheter electrodes 3 at least partially based on their correspondence to the simulated electrical field measurements 406 using their associated simulated spatial positions, and/or based on reference map 33. In some embodiments, position tracking results are output as position output data 414. In some embodiments, position data 414 are used (optionally, in conjunction with anatomical data 31 and/or other data for display) by display module 411 of user interface 50.

In some embodiments of the invention, simulated-to-actual track comparer 405 operates to determine spatial and/or electrical field measurement mappings between tracks 110 (comprising sequences of measurements taken from actual electrical field measurements 412), and corresponding reference tracks 111 (constructed from simulated electrical field measurements 406). The mappings are generated, for example, as described in relation to the flowcharts of FIGS. 1A-1B.

In some embodiments of the invention, the mappings are output as a calculated transform 408. In some embodiments, the calculated transform 408 not only registers actual and reference measurements along the tracks 111, 110; but also serves to register actual and reference measurements (measured values and reference values) of regions away from the tracks 111, 110. Optionally registration is anchored by known constraints away from the tracks, for example, voltages applied at positions of the body surface electrodes. Optionally, extrapolation is weighted for a factor reflecting distance from positions of actual measurement. For example, adjustments of the reference near positions of actual measurement bring about substantially complete correspondence to actual measurement, while adjustments further away are increasingly weighted toward the expectations of the references, and/or separately determined constraints.

Calculated transform 408 is optionally expressed and/or implemented at least partially as a geometrical transform of the reference intrabody positions of electrical field measurement values to a new set of intrabody positions. In some embodiments of the invention, the transform is selected so that electrical field measurements in a current procedure are mapped to corresponding reference electrical field values having reference positions which are consistent with known information about positions along the tracks which the electrical field measurements of the current procedure were taken from. For example, if a portion of a track is known to have taken place within the inferior vena cava, then the transform should be selected so that corresponding reference positions are also within the inferior vena cava.

In some embodiments, the calculated transform comprises terms for transformation of the reference field measurement value positions by linear scaling, rotation, and/or offset. Optionally, one or more of the scaling, rotation and offset are non-linear; for example, expressed as a higher-order polynomial, as a non-uniform deformation of a spatial mesh, or otherwise expressed.

Additionally or alternatively, the calculated transform 408 is expressed and/or implemented at least partially as a transform of the reference (and/or actual) electrical field measurement values themselves. For example, electrical field measurements are shifted, re-scaled, or otherwise transformed (linearly and/or non-linearly) so that positions of reference electrical field measurements corresponding to current-procedure measurements also satisfy known constraints on current-procedure measurement position (for example, position within particular regions of the vasculature and/or of the heart).

Optionally, both measurement values and measurement value positions are transformed, e.g., in a two-stage transformation. Different transformation methods can optionally make the anatomical space of the current procedure "look" like the reference anatomical space; alternatively or additionally, measurements from the reference anatomical space may be mapped into a space that resembles (as closely as can be determined from available data) anatomy of a body part navigated during the current procedure.

Optionally, as new electrical field measurements become available, the calculated transform 408 is updated by recalculation incorporating the new measurements. The updating measurements may be, but are not necessarily, also along tracks. Potential advantages of the use of tracks in particular as a basis for re-registration are described in relation to FIGS. 1A-1B.

In some embodiments of the invention, calculated transform 408 is used by simulation transformer 403 (FIG. 5) and/or reference map transformer 403A (FIG. 6) to update spatial registration between the positions at which actual electrical field measurements 412 are taken and corresponding simulated positions of simulated electrical field measurements 406.

Optionally, the update is iterative as calculated transform 408 is itself updated.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of calculating associations between intrabody catheter measurement values and positions within a body part, the method comprising:
   receiving a sequence of catheter-measured measurement values from at least one catheter, the measurements being measured using a sensor of the at least one catheter as it is moving, together with the catheter, along a measurement track within the body part;
   wherein the sequence of catheter-measured measurement values characterizes one or more characteristic features, each such feature comprising a pattern of measurement values ordered along the sequence, the measurement values being indicative of tissue environment along the measurement track; and
   determining a transform establishing correspondence between the characteristic features of the sequence of catheter-measured measurement values and characteristic features of an ordered set of reference values;
   wherein reference values of the ordered set of reference values are associated to positions along a predetermined reference track extending through a data representation of an anatomical space corresponding to the body part; and wherein, by said association, the transform allows the associating of intrabody catheter measurement values to positions within the body part; and
   associating further measurement values measured within the body part and away from the measurement track to positions in the data representation of the anatomical space, wherein the associating is based on:
   predetermined associations between additional reference values and additional respective positions within the data representation of the anatomical space, and
   the transform.

2. The method of claim 1, wherein the sequence of catheter-measured measurement values comprises electrical field measurement values measured from a catheter electrode moving along the measurement track through electrical fields induced within the body part; and wherein the reference values comprise reference electrical field values.

3. The method of claim 2, wherein the ordered set of reference electrical field values comprises one or more groups of reference electrical field values which indicate characteristic features of the induced electrical fields along the predetermined reference track.

4. The method of claim 2, wherein the electrical fields induced within the body part comprise electrical fields induced from electrodes placed at intrabody positions.

5. The method of claim 4, wherein the intrabody positions comprise positions within the coronary sinus.

6. The method of claim 2, wherein the electrical fields induced within the body part comprise electrical fields induced from body surface electrodes.

7. The method of claim 1, wherein the set of reference values is provided as a sequence of reference values associated with locations extending along the predetermined reference track.

8. The method of claim 1 wherein:
   the measurement track passes within a first blood vessel or heart chamber of a human; and
   the measurement values measured within the body part and away from the measurement track are measured within a second blood vessel or heart chamber of a human, different from but anatomically corresponding to the first.

9. The method of claim 1, wherein the determining a transform comprises:
   comparing the sequence of catheter-measured measurement values to ordered sets of reference values; and
   selecting one of said ordered sets of reference values for use as the ordered set of reference values which is in the correspondence with the sequence of catheter-measured measurement values established by the transform, based on the comparing.

10. The method of claim 9, further comprising: determining the transform based on the selected ordered set.

11. The method of claim 1, wherein the measurement values measured within the body part and away from the measurement track are measured within a lumen of a heart chamber distal from positions of the catheter along the measurement track.

12. The method of claim 1, wherein the ordered set of reference values comprises catheter-measured measurement values previously measured from at least one catheter.

13. The method of claim 12, wherein the previous measuring of the ordered set of reference values was during a same catheterization procedure as the measuring of the received sequence of catheter-measured measurement values.

14. The method of claim 12, wherein the previous measuring of the ordered set of reference values was during a catheterization procedure, different from a catheterization procedure during which the measuring of the sequence of catheter-measured measurement values were received.

15. The method of claim 1, wherein the ordered set of reference values comprises simulation values, the simulation values simulating measurements for positions within the data representation of the anatomical space.

16. The method of claim 1, wherein the electrical field measurement values measured within the body part and away from the measurement track are new measurements made after measurement along the measurement track.

17. The method of claim 1, wherein the associating uses electrical field measurement values obtained previously to the measurement along the measurement track.

18. The method of claim 17, wherein the reference values associated to positions within the data representation of the anatomical space comprise the previously obtained measurement values.

19. The method of claim 1, wherein the reference values of the ordered set of reference values are also associated to measurements of tissue state.

20. The method of claim 19, wherein the measurements of tissue state are measurements of tissue lesioning.

21. The method of claim 1, wherein the reference values of the ordered set of reference values are also associated to indications of previous ablation.

22. The method of claim 1, wherein the sequence of catheter-measured measurement values is measured from a plurality of crossing, time-varying electromagnetic fields.

23. The method of claim 1, comprising updating the transform, based on further received catheter-measured measurement values.

24. The method of claim 1, wherein the data representation of an anatomical space represents cardiovascular anatomy, and wherein the method comprises using the association of electrical field measurement values measured within the body part and away from the measurement track to positions in a data representation of the body part to guide navigation of the cardiovascular anatomy by the at least one catheter.

25. A system for associating measurement values to positions within a body part, the system comprising a processor, a memory storing data and a non-volatile memory storing instructions;
wherein the instructions, when executed, operate the processor to:
receive a sequence of catheter-measured measurement values from at least one catheter electrode moving along a measurement track within the body part;
wherein the sequence of catheter-measured measurement values characterizes one or more characteristic features, each comprising a pattern of measurement values ordered along the sequence, the measurement values being indicative of tissue environment along the measurement track; and
determine a transform establishing correspondence between the characteristic features of the sequence of catheter-measured measurement values and characteristic features of an ordered set of reference values;
wherein the reference values of the ordered set of reference values are associated to positions along a predetermined reference track extending through a data representation of an anatomical space corresponding to the body part, and wherein, by said association, and said transform, the system associates the measurement value to the positions within a body part; and
associate further measurement values measured within the body part and away from the measurement track to positions in the data representation of the anatomical space, wherein the associating is based on:
predetermined associations between additional reference values and additional respective positions within the data representation of the anatomical space, and
the transform.

26. A method of associating intrabody catheter measurement values to positions within a body part, the method comprising:
receiving a sequence of catheter-measured measurement values from at least one catheter, the measurements being measured using a sensor of the at least one catheter as the sensor is moving, together with the catheter, along a measurement track within the body part;
wherein the sequence of catheter-measured measurement values characterizes one or more characteristic features, each comprising a pattern of measurement values ordered along the sequence, the measurement values being indicative of tissue environment along the measurement track; and
determining a transform establishing correspondence between the characteristic features of the sequence of catheter-measured measurement values and characteristic features of an ordered set of reference values;
wherein reference values of the ordered set of reference values are associated to positions along a predetermined reference track extending through a data representation of an anatomical space corresponding to the body part, and wherein, by said association, the transform allows the associating of intrabody catheter measurement values to positions within the body part.

27. The method of claim 26, comprising:
associating measurement values measured within the body part and away from the measurement track to positions in the data representation of the anatomical space, wherein the associating is based on:
predetermined associations between reference values and positions within the data representation of the anatomical space, and
the transform.

28. The method of claim 2, wherein the electrical fields induced within the body part comprise electrical fields induced from electrodes placed at intrabody positions.

29. The method of claim 26, comprising using the transform to determine a position of an intrabody catheter measurement value at a location away from the measurement track.

* * * * *